(12) United States Patent
Stevis et al.

(10) Patent No.: US 11,479,802 B2
(45) Date of Patent: Oct. 25, 2022

(54) ASSAYS FOR SCREENING ACTIVITY OF MODULATORS OF MEMBERS OF THE HYDROXY STEROID (17-BETA) DEHYDROGENASE (HSD17B) FAMILY

(71) Applicant: Regeneron Pharmaceuticals, Inc., Tarrytown, NY (US)

(72) Inventors: Panayiotis Stevis, Tarrytown, NY (US); David Esopi, Tarrytown, NY (US); Jesper Gromada, Tarrytown, NY (US); Jorge Haller, Tarrytown, NY (US); Yashu Liu, Tarrytown, NY (US); Andrew Murphy, Tarrytown, NY (US); William Olson, Tarrytown, NY (US)

(73) Assignee: Regeneron Pharmaceuticals, Inc., Tarrytown, NY (US)

( * ) Notice: Subject to any disclaimer, the term of this patent is extended or adjusted under 35 U.S.C. 154(b) by 0 days.

(21) Appl. No.: 15/913,366

(22) Filed: Mar. 6, 2018

(65) Prior Publication Data

US 2018/0291422 A1    Oct. 11, 2018

Related U.S. Application Data

(60) Provisional application No. 62/484,141, filed on Apr. 11, 2017.

(51) Int. Cl.
| | |
|---|---|
| *C12Q 1/32* | (2006.01) |
| *C12Q 1/66* | (2006.01) |
| *C12N 9/96* | (2006.01) |
| *G01N 33/74* | (2006.01) |
| *C12N 9/04* | (2006.01) |

(52) U.S. Cl.
CPC ............ *C12Q 1/32* (2013.01); *C12N 9/0006* (2013.01); *C12N 9/96* (2013.01); *C12Q 1/66* (2013.01); *C12Y 101/01239* (2013.01); *G01N 33/743* (2013.01); *G01N 2500/02* (2013.01); *G01N 2500/04* (2013.01); *G01N 2500/10* (2013.01)

(58) Field of Classification Search
CPC .... C12Q 1/32; C12Q 1/66; C12Y 101/01239; C12N 9/96; C12N 9/0006; G01N 33/743; G01N 2500/04; G01N 2500/10; G01N 2500/02
See application file for complete search history.

(56) References Cited

U.S. PATENT DOCUMENTS

| | | | |
|---|---|---|---|
| 6,147,066 A * | 11/2000 | Petit ........................ | A61P 25/30 514/178 |
| 7,820,380 B2 | 10/2010 | Huang | |
| 7,951,382 B2 | 5/2011 | Gelber et al. | |
| 7,951,776 B2 | 5/2011 | Gelber | |
| 8,071,302 B2 | 12/2011 | Huang | |
| 8,945,847 B2 | 2/2015 | Benvenisty et al. | |
| 9,051,567 B2 | 6/2015 | Fitzgerald et al. | |
| 9,072,743 B2 | 7/2015 | Dilly et al. | |
| 9,328,346 B2 | 5/2016 | Lee et al. | |
| 9,375,433 B2 | 6/2016 | Dilly et al. | |
| 9,526,720 B2 | 12/2016 | Nagiec et al. | |
| 9,574,241 B2 | 2/2017 | Ferrando et al. | |
| 9,585,887 B2 | 3/2017 | Dilly et al. | |
| 9,585,890 B2 | 3/2017 | Dilly et al. | |
| 9,617,514 B2 | 4/2017 | Lunyak | |
| 9,629,804 B2 | 4/2017 | Heartlein et al. | |
| 9,632,090 B2 | 4/2017 | DePinho et al. | |
| 9,677,138 B2 | 6/2017 | Steiling et al. | |
| 9,796,762 B2 | 10/2017 | Kelly et al. | |
| 9,808,462 B2 | 11/2017 | Dilly et al. | |
| 9,816,094 B2 | 11/2017 | Lee et al. | |
| 10,052,284 B2 | 8/2018 | Heartlein et al. | |
| 10,577,630 B2 | 3/2020 | Zhang et al. | |
| 10,767,175 B2 | 9/2020 | Dellinger et al. | |
| 10,787,647 B2 | 9/2020 | Abul-Husn et al. | |
| 2003/0004102 A1 | 1/2003 | Ashkenazi | |
| 2005/0158376 A1 | 7/2005 | Sardi et al. | |

(Continued)

FOREIGN PATENT DOCUMENTS

| | | |
|---|---|---|
| CN | 104698108 A * | 6/2015 |
| CN | 103520724 B | 5/2016 |

(Continued)

OTHER PUBLICATIONS

CN 104698108 Machine Translation. Published Jun. 10, 2015. (Year: 2015).*

Leippe, D. Bioluminescent Nicotinamide Adenine Dinucleotide Detection Assays Part I: Technology and Features. [Internet] Sep. 2014. (tpub_150). Accessed Jan. 31, 2020. Available from: http://www.promega.com/resources/pubhub/bioluminescent-nicotinamide-adenine-dinucleotide-detection-assays/). (Year: 2014).*

(Continued)

*Primary Examiner* — Renee Claytor
*Assistant Examiner* — Susan E. Fernandez
(74) *Attorney, Agent, or Firm* — Armstrong Teasdale LP

(57) ABSTRACT

Screening methods as well as kits for identifying modulators of hydroxysteroid (17-beta) dehydrogenase (HSD17B) family member proteins, such as HSD17B13, are provided. The methods comprise screening molecules for their capacity to modulate the HSD17B family member protein, including inhibiting the HSD17B family member protein, as measured by substrate depletion, product concentration from the HSD17B family member protein substrate conversion or NADH concentration, levels of labeled substrate, luciferin light emission, or combinations thereof. Inhibitors of HSD17B family member proteins identified through the screening methods may be used to treat liver diseases, disorders, or conditions in which the HSD17B family member protein plays a role.

7 Claims, 15 Drawing Sheets

Specification includes a Sequence Listing.

(56) References Cited

U.S. PATENT DOCUMENTS

| | | | |
|---|---|---|---|
| 2007/0219169 A1* | 9/2007 | Becourt | A61K 31/565 514/170 |
| 2008/0300170 A1 | 12/2008 | Gelber et al. | |
| 2009/0169585 A1 | 7/2009 | Sardi | |
| 2009/0203602 A1 | 8/2009 | Gelber et al. | |
| 2010/0028879 A1* | 2/2010 | Labrie | C12Q 1/32 435/6.16 |
| 2010/0056384 A1 | 3/2010 | Hobbs et al. | |
| 2010/0209427 A1 | 8/2010 | Li et al. | |
| 2010/0266618 A1 | 10/2010 | Stojdl et al. | |
| 2010/0267052 A1 | 10/2010 | Gelber et al. | |
| 2011/0130442 A1 | 6/2011 | Kosaka et al. | |
| 2011/0262462 A1 | 10/2011 | Platt et al. | |
| 2011/0129831 A1 | 12/2011 | Cargill et al. | |
| 2012/0015904 A1 | 1/2012 | Sharp et al. | |
| 2012/0028816 A1 | 2/2012 | Warren et al. | |
| 2012/0058088 A1 | 3/2012 | Sardi | |
| 2012/0276528 A1 | 11/2012 | Cargill et al. | |
| 2013/0005596 A1 | 1/2013 | Gong et al. | |
| 2013/0029873 A1 | 1/2013 | de Perrot et al. | |
| 2013/0079241 A1 | 3/2013 | Luo et al. | |
| 2013/0237454 A1 | 9/2013 | Schutzer | |
| 2013/0309769 A1 | 11/2013 | Benvenisty et al. | |
| 2014/0004153 A1 | 1/2014 | Cowing et al. | |
| 2014/0011889 A1 | 1/2014 | Sardi | |
| 2014/0045915 A1 | 2/2014 | Skog et al. | |
| 2014/0057800 A1 | 2/2014 | Brattbakk et al. | |
| 2014/0072957 A1 | 3/2014 | Huang et al. | |
| 2014/0088120 A1* | 3/2014 | Dilly | A61P 17/08 514/259.41 |
| 2014/0163118 A1 | 6/2014 | Giuliani et al. | |
| 2014/0179536 A1 | 6/2014 | Hobbs et al. | |
| 2014/0295425 A1 | 10/2014 | Nagy | |
| 2014/0329704 A1 | 11/2014 | Melton et al. | |
| 2014/0363502 A1 | 12/2014 | Sardi | |
| 2014/0378425 A1 | 12/2014 | Wilde et al. | |
| 2015/0050728 A1 | 2/2015 | Benvenisty et al. | |
| 2015/0079061 A1 | 3/2015 | Casey et al. | |
| 2015/0079062 A1 | 3/2015 | Casey et al. | |
| 2015/0366997 A1 | 12/2015 | Guild et al. | |
| 2016/0024498 A1 | 1/2016 | Fitzgerald et al. | |
| 2016/0030585 A1 | 2/2016 | Barnes et al. | |
| 2016/0032388 A1 | 2/2016 | Huang et al. | |
| 2016/0032395 A1 | 2/2016 | Davicioni et al. | |
| 2016/0184458 A1 | 6/2016 | Heartlein et al. | |
| 2016/0237501 A1 | 8/2016 | Sharp et al. | |
| 2016/0320395 A1 | 11/2016 | Ward et al. | |
| 2016/0355806 A1 | 12/2016 | Lee et al. | |
| 2016/0355813 A1 | 12/2016 | Lee et al. | |
| 2016/0376598 A1 | 12/2016 | Lee et al. | |
| 2017/0022504 A1 | 1/2017 | Lee et al. | |
| 2017/0037396 A1 | 2/2017 | Lee et al. | |
| 2017/0044550 A1 | 2/2017 | Lee et al. | |
| 2017/0247758 A1 | 8/2017 | Spiller et al. | |
| 2017/0247759 A1 | 8/2017 | Wilde et al. | |
| 2017/0283770 A1 | 10/2017 | Lunyak | |
| 2017/0335396 A1 | 11/2017 | Kennedy et al. | |
| 2017/0340661 A1 | 11/2017 | Fitzgerald et al. | |
| 2017/0349903 A1 | 12/2017 | Liu et al. | |
| 2017/0356002 A1 | 12/2017 | Thompson et al. | |
| 2018/0179553 A1 | 6/2018 | Watson et al. | |
| 2018/0179593 A1 | 6/2018 | Melton et al. | |
| 2018/0185516 A1 | 7/2018 | Ansell et al. | |
| 2018/0201936 A1 | 7/2018 | Hinkle | |
| 2018/0216084 A1 | 8/2018 | Abul-Husn et al. | |
| 2018/0216104 A1 | 8/2018 | Abul-Husn et al. | |
| 2018/0273955 A1 | 9/2018 | Fitzgerald et al. | |
| 2019/0002869 A1 | 1/2019 | Yin et al. | |
| 2019/0316121 A1 | 10/2019 | Smith et al. | |
| 2019/0365924 A1 | 12/2019 | Conway et al. | |
| 2019/0390195 A1 | 12/2019 | Tondera et al. | |
| 2020/0354693 A1 | 11/2020 | Abul-Husn et al. | |

FOREIGN PATENT DOCUMENTS

| | | |
|---|---|---|
| EP | 3011032 | 10/2019 |
| EP | 3620524 | 3/2020 |
| EP | 3011031 | 9/2020 |
| RU | 2545990 | 4/2015 |
| RU | 2562868 | 9/2015 |
| WO | 1995029255 | 11/1995 |
| WO | 9720942 | 6/1997 |
| WO | 1999046279 | 9/1999 |
| WO | 2004110459 | 12/2004 |
| WO | 2005108415 | 11/2005 |
| WO | 2009039195 | 3/2009 |
| WO | 2010028110 | 3/2010 |
| WO | 2010040571 | 4/2010 |
| WO | 2010064702 | 6/2010 |
| WO | 2011006214 | 1/2011 |
| WO | 2011084747 | 7/2011 |
| WO | 2012052953 | 4/2012 |
| WO | 2012087983 | 6/2012 |
| WO | 2013126565 | 8/2013 |
| WO | 2013176772 | 11/2013 |
| WO | 2013177060 | 11/2013 |
| WO | 2013190075 | 12/2013 |
| WO | 2013166264 | 1/2014 |
| WO | 2014089313 | 6/2014 |
| WO | 2014196957 | 12/2014 |
| WO | 2015169971 | 11/2015 |
| WO | 2016004387 | 1/2016 |
| WO | 2016009246 | 1/2016 |
| WO | 2017048620 | 3/2017 |
| WO | 2017106210 | 6/2017 |
| WO | 2017106283 | 6/2017 |
| WO | 2017106292 | 6/2017 |
| WO | 2017106364 | 6/2017 |
| WO | 2017106370 | 6/2017 |
| WO | 2017106375 | 6/2017 |
| WO | 2017106382 | 6/2017 |
| WO | 2017156310 | 9/2017 |
| WO | 2017191274 | 11/2017 |
| WO | 2017211947 | 12/2017 |
| WO | 2018107026 | 6/2018 |
| WO | 2018107028 | 6/2018 |
| WO | 2018136702 | 7/2018 |
| WO | 2018136758 | 7/2018 |
| WO | 2018220211 | 12/2018 |
| WO | 2019183164 | 9/2019 |
| WO | 2019183329 | 9/2019 |
| WO | 2019237069 | 12/2019 |
| WO | 2019246203 | 12/2019 |

OTHER PUBLICATIONS

CN 103520724 Machine Translation. Published Jan. 22, 2014 (Year: 2014).*

Moeller, G et al. Multifunctionality of human 17beta-hydroxysteroid dehydrogenases. Molecular and Cellular Endocrinology. 2006. 248: 47-55. (Year: 2006).*

Su, W et al. Comparative proteomic study reveals 17beta-HSD13 as a pathogenic protein in nonalcoholic fatty liver disease. PNAS. 2014. 111(31): 11437-11442. (Year: 2014).*

Labrie, F. Multiple intracrine hormonal targets in the prostate: opportunities and challenges. BJU Int. 2007. 100 (Supplement 2): 48-51. (Year: 2007).*

Mashek, DG et al. Hepatic lipid droplet biology: getting to the root of fatty liver. Hepatology. 2015. 62(3): 964-967. (Year: 2015).*

Ducharme, NA et al. Minireview: lipid droplets in lipogenesis and lipolysis. Endocrinology. 2008. 149(3): 942-949. (Year: 2008).*

Wolf, MS et al. To err is human: patient misinterpretations of prescription drug label instructions. Patient Education and Counseling. 2007. 67: 293-300. (Year: 2007).*

Karlson, P. Chapter V. in: Introduction to Modern Biochemistry (fourth edition). 1975. Academic Press, New York, New York, pp. 74-100. (Year: 1975).*

Jequier, E et al. Water as an essential nutrient: the physiological basis of hydration. European Journal of Clinical Nutrition. 2010. 64: 115-123. (Year: 2010).*

(56) References Cited

OTHER PUBLICATIONS

Doan, TB et al. Breast cancer prognosis predicted by nuclear receptor-coregulator networks. Molecular Oncology. 2014. 8: 998-1013. (Year: 2014).*
Kuhl, H. Pharmacology of estrogens and progestagens: influence of different routes of administration. Climacteric. 2005. 8(Suppl 1): 3-63. (Year: 2005).*
Brooks, HB et al. Basics of Enzymatic Assays for HTS. May 1, 2012 [Updated Oct. 1, 2012], In: Markossian et al., editors. Assay Guidance Manual [Internet], Bethesda (MD): Eli Lilly & Company and the National Center for Advancing Translational Sciences; 2004-. (Year: 2012).*
Elphick, LM et al. Conserved valproic-acid-induced lipid droplet formation in Dictyostelium and human hepatocytes identifies structurally active compounds. Disease Models & Mechanisms. 2012. 5: 231-240. (Year: 2012).*
Adam, M., et al., "Hydroxysteroid (17b) dehydrogenase 13 deficiency triggers hepatic steatosis and inflammation in mice", The FASEB Journal, 2018, pp. 1-14.
Altschul, S. F., et al., "Basic Local Alignment Search Tool", J. Mol. Biol., 1990, pp. 403-410, 215.
Altschul, S. F., et al., "Gapped BLAST and PSI-BLAST: a new generation of protein database search programs", Nucleic Acids Research, 1997, pp. 3389-3402, 25 (17).
Brasaemle, D. L., et al., "Isolation of Lipid Droplets from Cells by Density Gradient Centrifugation", Current Protocols in Cell Biology, 2005, 3.15.1-3.15.12.
Browning, J. D., et al., "Prevalence of Hepatic Steatosis in an Urban Population in the United States: Impact of Ethnicity", Hepatology, 2004, pp. 1387-1395, 40(6).
Chambers, J. C., et al., "Genome-wide association study identifies loci influencing concentrations of liver enzymes in plasma" Nat Genet, 2011, pp. 1131-1138, 43(11).
Cohen, J. C., et al., "Human Fatty Liver Disease: Old Questions and New Insights", Science, 2011, pp. 1519-1523, 332.
Denny, J. C., et al., "PheWAS: demonstrating the feasibility of a phenome-wide scan to discover gene-disease associations", Bioinformatics, 2010, pp. 1205-1210, 26(9).
Denny, J. C., et al., "Systematic comparison of phenome-wide association study of electronic medical record data and genome-wide association study data", Nat Biotechnol, 2013, pp. 1102-1110, 31(12).
Dewey, F. E., et al., "Distribution and clinical impact of functional variants in 50,726 whole-exome sequences from the DiscovEHR Study", Science, 2016, pp. aaf6814, 354(6319).
Ding, Y., et al., "Isolating lipid droplets from multiple species", Nature Protocols, 2013, pp. 43-51, 8(1).
Kampf, C., et al., "The human liver-specific proteome defined by transcriptomics and antibody-based profiling", The FASEB Journal, 2014, pp. 2901-2914, 28(7).
Kleiner, D. E., et al., "Design and Validation of a Histological Scoring System for Nonalcoholic Fatty Liver Disease", Hepatology, 2005, pp. 1313-1321, 41(6).
Kochanek, K. D., et al., "Deaths: Final Data for 2014", National Viral Statistics Reports, 2016, pp. 1-122, 65(4).
Kozlitina, J., et al., "Exome-wide association study identifies a TM6SF2 variant that confers susceptibility to nonalcoholic fatty liver disease", Nat Genet, 2014, pp. 352-356, 46(4).
Lazo, M., et al., "Prevalence of Nonalcoholic Fatty Liver Disease in the United States: The Third National Health and Nutrition Examination Survey, 1988-1994", Am J Epidemiol, 2013, pp. 38-45, 178(1).
Li, H., et al., "Fast and accurate short read alignment with Burrows-Wheeler transform", Bioinformatics, 2009, pp. 1754-1760, 25(14).
Li, P., et al., "LTB4 causes macrophage-mediated inflammation and directly induces insulin resistance in obesity", Nat Med, 2015, pp. 239-247, 21(3).
Liu, S., et al., "Molecular cloning and expression analysis of a new gene for shortchain dehydrogenase/reductase 9", Acta Biochimica Polonica, 2007, pp. 213-218, 54(1).
Liu, Y.-L., et al., "TM6SF2 rs58542926 influences hepatic fibrosis progression in patients with non-alcoholic fatty liver disease", Nature Communications, 2014, pp. 1-6, 5(4309).
McKenna, A., et al., "The Genome Analysis Toolkit: A MapReduce framework for analyzing next-generation DNA sequencing data", Genome Research, 2010, pp. 1297-1303, 20.
Moeller, G., et al., "Integrated view on 17betahydroxysteroid dehydrogenases", Molecular and Cellular Endocrinology, 2009, pp. 7-19, 301.
Morgan, R. L., et al., "Eradication of Hepatitis C Virus Infection and the Development of Hepatocellular Carcinoma", Annals of Internal Medicine, 2013, pp. 329-337 and W-158-W-160, 158(5)(Part 1).
NCBI Reference Sequence: NM_178135, "*Homo spiens* hydroxysteroid 17-beta dehydrogenase 13 (HSD17B13), transcript variant A, mRNA" 2017, pp. 1-5.
NCBI Reference Sequence: NM_001136230, "*Homo sapiens* hydroxysteroid 17-beta dehydrogenase 13 (HSD17B13), transcript variant B, mRNA" 2017, pp. 1-5.
NCBI Reference Sequence: NP_835236, "17-beta-hydroxysteroid dehydrogenase 13 isoform A precursor [*Homo sapiens*]", 2017 pp. 1-4.
NCBI Reference Sequence: NP_001129702, "17-beta-hydroxysteroid dehydrogenase 13 isoform B [*Homo sapiens*]", 2017, pp. 1-4.
Pruim, R. J., et al., "LocusZoom: regional visualization of genome-wide association scan results", Bioinformatics, 2010, pp. 2336-2337, 26(18).
Reid, J. G., et al., "Launching genomics into the cloud: deployment of Mercury, a next generation sequence analysis pipeline", BMC Bioinformatics, 2014, pp. 1-11, 15(30).
Romeo, S., et al., "Genetic variation in PNPLA3 confers susceptibility to nonalcoholic fatty liver disease", Nat Genet, 2008, pp. 1461-1465, 40(12).
Rotman, Y., et al., "The Association of Genetic Variability in PNPLA3 with Histological Severity of Non-Alcoholic Fatty Liver Disease", Hepatology, 2010, pp. 894-903, 52(3).
Smith, T. F., et al., "Comparsion of Biosequences", Advances in Applied Mathematics, 1981, pp. 482-489, 2.
Sookoian, S., et al., "A nonsynonymous gene variant in the adiponutrin gene is associated with nonalcoholic fatty liver disease severity", Journal of Lipid Research, 2009, pp. 2111-2116, 50.
Sookoian, S., et al., "Genetic Variation in Transmembrane 6 Superfamily Member 2 and the Risk of Nonalcoholic Fatty Liver Disease and Histological Disease Severity", Hepatology, 2015, pp. 515-525, 61(2).
Epeliotes, E. K., et al., "Genome-Wide Association Analysis Identifies Variants Associated with Nonalcoholic Fatty Liver Disease That Have Distinct Effects on Metabolic Traits", PLoS Genetics, 2011, e1001324, 7(3).
Su, W., et al., "Comparative proteomic study reveals 17I-HSD13 as a pathogenic protein in nonalcoholic fatty liver disease", PNAS, 2014, pp. 11437-11442, 111(31).
Trepo, E., et al., "PNPLA3 gene in liver diseases", Journal of Hepatology, 2016, pp. 399-412, 65.
UniProtKB-Q7Z5P4-1, "17-beta-hydroxysteroid dehydrogenase 13", 2003, pp. 6.
UniProtKB-Q7Z5P4-2, "17-beta-hydroxysteroid dehydrogenase 13", 2003, pp. 6-7.
Van Der Meer, A. J., et al., "Association Between Sustained Virological Response and All-Cause Mortality Among Patients With Chronic Hepatitis C and Advanced Hepatic Fibrosis", JAMA, 2012. pp. 2584-2593, 308(24).
Victor, R. G., et al., "The Dallas Heart Study: A Population-Based Probability Sample for the Multidisciplinary Study of Ethnic Differences in Cardiovascular Health", Am J Cardiol, 2004, pp. 1473-1480, 93.
Willer, C. J., et al., "METAL: fast and efficient meta-analysis of genomewide association scans", Bioinformatics, 2010, pp. 2190-2191, 26(17).
Williams, C. D., et al., "Clinical Advances in Liver, Pancreas, and Biliary Tract", Gastroenterology, 2011, pp. 124-131, 140.

(56) References Cited

OTHER PUBLICATIONS

Wong, R. J., et al., "Nonalcoholic Steatohepatitis Is the Second Leading Etiology of Liver Disease Among Adults Awaiting Liver Transplantation in the United States", Gastroenterology, 2015, pp. 547-555, 148.

Yang, J., et al., "GCTA: A Tool for Genome-wide Complex Trait Analysis", The American Journal of Human Genetics, 2011, pp. 76-82, 88.

Younossi, Z. M., et al., "Changes in the Prevalence of the Most Common Causes of Chronic Liver Diseases in the United States From 1988 to 2008", Clinical Gastroenterology and Hepatology, 2011, pp. 524-530, 9.

Yuan, X., et al., "Population-Based Genome-wide Association Studies Reveal Six Loci Influencing Plasma Levels of Liver Enzymes", The American Journal of Human Genetics, 2008, pp. 520-528, 83.

Zhang, J., et al., "PowerBLAST: A New Network BLAST Application for Interactive of Automated Sequence Analysis and Annotation", Genome Research, 1997, pp. 649-656, 7.

International Search Report/Written Opinion dated Jun. 26, 2019 received in application No. PCT/US19/23079.

G. Sivan et al., "Identification of Restriction Factors by Human Genome-Wide RNA Interference Screening of Viral Host Range Mutants Exemplified by Discovery of SAMD9 and WDR6 as Inhibitors of the Vaccinia Virus K1L-C7L-Mutant", mBIO, 2015, 6(4):e01122-15.

S.Q. Tsai and K. Young, "Defining and improving the genome-wide specificities of CRISPR-Cas9 nucleases", Nature Reviews Genetics, 2016, 17:300-312.

Official Action dated Jun. 12, 2019 issued in related U.S. Appl. No. 15/875,192.

RefSNP cluster report rs72613567 (printed Jun. 6, 2019 from ncbi.nlm.nih.gov).

GenBank accession DR004209 (submitted Jan. 2011, printed Jun. 10, 2019, from ncbi.nlm.nih.gov).

PROMEGA "Technical Manual: NAD(P)H-Glo Detection System", 2017, TM398, pp. 1-15.

Abul-Husn et al., "A Protein-Truncating HSD17B13 Variant and Protection from Chronic Liver Disease", N Engl J Med, 2018, 378, pp. 1096-1106.

Ford et al., "A New Assay for Picomole Levels of Androsterone and Testosterone Using Co-immobilized Luciferase, Oxidoreductase, and Steroid Dehydrogenase", Analytical Biochemistry, 1981, 110, pp. 43-48.

Krazeisen et al., "Phytoestrogens inhibit human 17β-hydroxysteroid dehydrogenase type 5", Molecular and Cellular Endocrinology, 2001, 171, pp. 151-162.

Edelman et al., "Genetic analysis of nonalcoholic fatty liver disease within a Caribbean-Hispanic population", Molecular Genetics & Genomic Medicine, 2015, 3(6), pp. 558-569.

Hotta et al., "R association of the rs738409 polymorphism in PNPLA3 with liver damage and the development of nonalcoholic fatty liver disease", BMC Medical Genetics, 2010, 11(172), pp. 1-10.

Kahali et al., "Insights from Genome-Wide Association Analyses of Nonalcoholic Fatty Liver Disease", Seminars in Liver Disease, 2015, 35(4), pp. 375-391.

Oniki et al., "Influence of the PNPLA3 rs738409 Polymorphism on Non-Alcoholic Fatty Liver Disease and Renal Function among Normal Weight Subjects", Plos One, 2015, 10(7), pp. e0132640.

Shen et al., "The rs738409 (I148M) variant of the PNPLA3 gene and cirrhosis: a meta-analysis", Journal of Lipid Research, 2015, 56(1), pp. 167-175.

Brantly et al., "Crystal RG. Molecular basis of alpha-1-antitrypsin deficiency", Am J Med, 1988, pp. 13-31, 84.

Feitosa et al., "The ERLIN1-CHUK-CWF19L1 gene cluster influences liver fat deposition and hepatic inflammation in the NHLBI Family Heart Study", Atherosclerosis, 2013, pp. 175-180, 228.

Huang et al., "Expression and Characterization of a PNPLA3 Protein Isoform (I148M) Associated with Nonalcoholic Fatty Liver Disease", J Biol Chem, 2011, pp. 37085-37093, 286.

Kitamoto et al., "Genome-wide scan revealed that polymorphisms in the PNPLA3, SAMM50, and PARVB genes are associated with development and progression of nonalcoholic fatty liver disease in Japan", Hum Genet, 2013, pp. 783-792, 132.

Mahdessian et al., "TM6SF2 is a regulator of liver fat metabolism influencing triglyceride secretion and hepatic lipid droplet content", PNAS, 2014, pp. 8913-8918, 111.

Pirazzi et al., "Patatin-like phospholipase domain-containing 3 (PNPLA3) I148M (rs738409) affects hepatic VLDL secretion in humans and in vitro", J Hepatol, 2012, pp. 1276-1282, 57.

Shen et al., "The rs738409 (I148M) variant of the PNPLA3 gene and cirrhosis: a meta-analysis", J Lipid Res, 2015, pp. 167-175, 56.

Smagris et al., "Inactivation of Tm6sf2, a Gene Defective in Fatty Liver Disease, Impairs Lipidation but Not Secretion of Very Low Density Lipoproteins", J Biol Chem, 2016, pp. 10659-10676, 291.

International Search Report and Written Opinion for PCT Application PCT/US2018/014357.

New England Biolabs Catalog, "Nucleic Acids, Linkers and Primers", 1998/199, pp. 121 and 284.

Schiavinato et al., "EMILIN-3, Peculiar Member of Elastin Microfibril Interface-located Protein (EMILIN) Family, Has Distinct Expression Pattern, Forms Oligomeric Assemblies, and Serves as Transforming Growth Factor B (TGF-B) Antagonist", Journal of Biological Chemistry, 2012, 187(14), pp. 11498-11515.

SNP(ss) Report in Submission Format for NCBI Assay Id (ss#): ss557289122, 2012, www.ncbi.nlm.gov/.

Non-Final Office Action dated Mar. 12, 2020 in related U.S. Appl. No. 15/875,192.

Ghanbari, et al., "Genetic Variations in MicroRNA-Binding Sites Affect MicroRNA-Mediated Regulation of Several Genes Associated With Cardio-metabolic Phenotypes," Circ. Cardiovasc. Genet., 2015, 8(3), pp. 473-486.

Gieger, et al., "New gene functions in megakaryopoiesis and platelet formation," Nature, 2012, 480(7376), pp. 201-208 plus Supplementary Information.

Haapaniemi et al., "CRISPR-Cas9 genome editing induces a p53-mediated DNA damage response," Nat. Med. doi: 10.1038/s41591-018-0049-z, (Jun. 11, 2018, epub ahead of print).

Ihry et al., "p53 inhibits CRISPR-Cas9 engineering in human pluripotent stem cells," Nat. Med. doi: 10.1038/s41591-018-0050-6 (Jun. 11, 2018, epub ahead of print).

Jiang et al., "Structural Biology. A Cas9-guide RNA complex preorganized for target DNA recognition," Science, 2015, 348(6242), pp. 1477-1481.

Jinek et al., "RNA-programmed genome editing in human cells," eLife, 2013, 2:e00471.

Komor et al., "CRISPR-Based Technologies for the Manipulation of Eukaryotic Genomes," Cell, 2017, 168(1-2), pp. 20-36.

Kosicki et al., "Repair of double-strand breaks induced by CRISPR-Cas9 leads to large deletions and complex rearrangements," Nat. Biotechnol., 2018, 36(8), pp. 765-771.

Nishimasu et al., "Crystal Structure of Cas9 in Complex with Guide RNA and Target DNA," Cell, 2014, 156(5), pp. 935-949.

PubMed NCBI Search Results for ((CRISPR[Title] or Cas9[Title]) and ("Jan. 1, 2012"[PDATE]: "Jan. 22, 2017")), https://www.ncbi.nlm.nih.gov/pubmed, retrieved on Sep. 22, 2019.

Quadri, et al., "Mutations in SLC30A10 Cause Parkinsonism and Dystonia with Hypermanganesemia, Polycthemia, and Chronic Liver Disease," The American Journal of Human Genetics, 2012, 90, pp. 467-477 plus Supplemental Material.

Ratziu, et al., "Current efforts and trends in the treatment of NASH," Journal of Hepatology, 2015, 62, pp. S65-S75.

Santa Cruz Biotechnology, "17ß-HSD13 Antibody (K-14): sc-161285" [Retrieved from the Internet Jun. 1, 2016: www.scbt.com/datasheet-161285-17betahsd13-k-14-antibody.html].

Santa Cruz Biotechnology, "17ß-HSD13 siRNA (m), shRNA and Lentiviral Particle Gene Silencers" [Retrieved from the ntemet Jun. 1, 2016: www.scbt.com/datasheet-108263-17beta-hsd13-sima-m.html].

Tang, et al., "A mouse knockout library for secreted and transmembrane proteins," Nature Biotechnology, 2010, 28 (7), pp. 749-755 plus Online Methods and Supplementary Information.

(56) References Cited

OTHER PUBLICATIONS

Non-Final Office Action dated Jul. 10, 2019 for U.S. Appl. No. 15/875,514.
Notice of Allowance dated Jan. 22, 2020 in U.S. Appl. No. 15/875,514.
International Search Report and Written Opinion of the International Searching Authority dated Jun. 6, 2018 for WIPO Application No. PCT/US2018/014454.
Business Wire, "Arrowhead Pharmaceuticals Initiates Phase 1/2 Study of ARO-HSD in Normal Healthy Volunteers and Patients with NASH of Suspected NASH", Mar. 3, 2020, pp. 1-2. businesswire.com/news/home/20200303005396/en/Arrowhead-Pharmaceuticals-Initiates-Phase-12-Study-ARO-HSD.
Zhang et al., "Omic studies reveal the pathogenic lipid droplet proteins in non-alcoholic fatty liver disease", Protein Cell, 2017, 8(1), pp. 4-13.
Non-Final Office Action dated Jun. 12, 2020 for U.S. Appl. No. 16/157,503.
Notice of Allowance dated May 1, 2020 in U.S. Appl. No. 15/875,514.
Final Office Action dated Dec. 3, 2020 for U.S. Appl. No. 15/875,192.
Notice of Allowance dated Nov. 19, 2020 for U.S. Appl. No. 16/157,503.
Kitamoto et al., "Association of polymorphisms in GCKR and TRIB1 with nonalcoholic fatty liver disease and metabolic syndrome traits", Endocrine Journal, 2014, 61(7), pp. 683-689.
Anstee et al., "Genetic Factors That Affect Risk of Alcoholic and Nonalcoholic Fatty Liver Disease", Gastroenterology, 2016, 150(8), pp. 1728-1744.
Non-Final Office Action dated Feb. 4, 2022 for U.S. Appl. No. 15/875,192.
Rao et al., "Genotyping single nucleotide polymorphisms directly from genomic DNA by invasive cleavage reaction on microspheres", Nucleic Acids Research, 2003, 31(11), pp. 1-8.
Stevens et al., "Analysis of single nucleotide polymorphisms with solid phase invasive cleavage reactions", Nucleic Acid Research, 2001, 29(16), pp. 1-8.
Hassan et al., "Nonalcoholic fatty liver disease: A comprehensive review of a growing epidemic", World J Gastroenterology, 2014, 20(34), pp. 12082-12101.
Nemudryi et al., "TALEN and CRISPR/Cas Genome Editing Systems: Tools of Discovery", Acta Nature, 2014, 6 (No. 3 (22)), pp. 19-40.
Sun et al., "The CRSPR/Cas9 system for gene editing and its potential application in pain research", Transl Perioper Pain Med, 2016, 1(3), pp. 22-33.
Third Party Submission filed Feb. 25, 2022 in U.S. Appl. No. 16/978,947.
Del Ben et al., "Non-alcoholic fatty liver disease, metabolic syndrome and patatin-like phospholipase domain-containing protein3 gene variants", European Journal of Internal Medicine, 2014, 25, pp. 566-570.

* cited by examiner

```
                        SEQUENCE LISTING

<160> NUMBER OF SEQ ID NOS: 9

<210> SEQ ID NO 1
<211> LENGTH: 300
<212> TYPE: PRT
<213> ORGANISM: artificial sequence
<220> FEATURE:
<223> OTHER INFORMATION: Isoform A

<400> SEQUENCE: 1

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Phe
            260                 265                 270

Leu Pro Glu Arg Ala Ser Ala Ile Leu Asn Arg Met Gln Asn Ile Gln
        275                 280                 285
```

```
Phe Glu Ala Val Val Gly His Lys Ile Lys Met Lys
    290                 295                 300

<210> SEQ ID NO 2
<211> LENGTH: 264
<212> TYPE: PRT
<213> ORGANISM: artificial sequence
<220> FEATURE:
<223> OTHER INFORMATION: Isoform B

<400> SEQUENCE: 2

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
                35                  40                  45

Gly Arg Gln Thr Thr Tyr Glu Phe Ala Lys Arg Gln Ser Ile Leu Val
            50                  55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
            100                 105                 110

Phe Trp Ile Thr Lys Ala Leu Leu Pro Ser Met Met Glu Arg Asn His
            115                 120                 125

Gly His Ile Val Thr Val Ala Ser Val Cys Gly His Glu Gly Ile Pro
        130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
                165                 170                 175

Thr Ser Cys Leu Cys Pro Val Phe Val Asn Thr Gly Phe Thr Lys Asn
            180                 185                 190

Pro Ser Thr Arg Leu Trp Pro Val Leu Glu Thr Asp Glu Val Val Arg
        195                 200                 205

Ser Leu Ile Asp Gly Ile Leu Thr Asn Lys Lys Met Ile Phe Val Pro
    210                 215                 220

Ser Tyr Ile Asn Ile Phe Leu Arg Leu Gln Lys Phe Leu Pro Glu Arg
225                 230                 235                 240

Ala Ser Ala Ile Leu Asn Arg Met Gln Asn Ile Gln Phe Glu Ala Val
                245                 250                 255

Val Gly His Lys Ile Lys Met Lys
            260

<210> SEQ ID NO 3
<211> LENGTH: 261
<212> TYPE: PRT
<213> ORGANISM: artificial sequence
<220> FEATURE:
<223> OTHER INFORMATION: Isoform C

<400> SEQUENCE: 3

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
```

```
                20                  25                  30
Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Phe Leu Pro Glu Arg Ala Ser Ala
225                 230                 235                 240

Ile Leu Asn Arg Met Gln Asn Ile Gln Phe Glu Ala Val Val Gly His
                245                 250                 255

Lys Ile Lys Met Lys
            260

<210> SEQ ID NO 4
<211> LENGTH: 274
<212> TYPE: PRT
<213> ORGANISM: artificial sequence
<220> FEATURE:
<223> OTHER INFORMATION: Isoform D

<400> SEQUENCE: 4

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
        35                  40                  45

Gly Arg Gln Thr Thr Tyr Glu Phe Ala Lys Arg Gln Ser Ile Leu Val
    50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
```

```
                115                 120                 125
Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys Val
            260                 265                 270

Ser Ser

<210> SEQ ID NO 5
<211> LENGTH: 324
<212> TYPE: PRT
<213> ORGANISM: artificial sequence
<220> FEATURE:
<223> OTHER INFORMATION: Isoform E

<400> SEQUENCE: 5

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Asn Gly Lys Asp Ile Arg Ser Asn Tyr Leu
145                 150                 155                 160

Asp Val Tyr Arg Ile Glu Asp Thr Phe Gly Arg Asp Ser Glu Ile Thr
                165                 170                 175

Lys Ala Leu Leu Pro Ser Met Met Glu Arg Asn His Gly His Ile Val
            180                 185                 190

Thr Val Ala Ser Val Cys Gly His Glu Gly Ile Pro Tyr Leu Ile Pro
        195                 200                 205
```

```
Tyr Cys Ser Ser Lys Phe Ala Ala Val Gly Phe His Arg Gly Leu Thr
            210                 215                 220

Ser Glu Leu Gln Ala Leu Gly Lys Thr Gly Ile Lys Thr Ser Cys Leu
225                 230                 235                 240

Cys Pro Val Phe Val Asn Thr Gly Phe Thr Lys Asn Pro Ser Thr Arg
                245                 250                 255

Leu Trp Pro Val Leu Glu Thr Asp Glu Val Val Arg Ser Leu Ile Asp
                260                 265                 270

Gly Ile Leu Thr Asn Lys Lys Met Ile Phe Val Pro Ser Tyr Ile Asn
            275                 280                 285

Ile Phe Leu Arg Leu Gln Lys Phe Leu Pro Glu Arg Ala Ser Ala Ile
        290                 295                 300

Leu Asn Arg Met Gln Asn Ile Gln Phe Glu Ala Val Val Gly His Lys
305                 310                 315                 320

Ile Lys Met Lys

<210> SEQ ID NO 6
<211> LENGTH: 284
<212> TYPE: PRT
<213> ORGANISM: artificial sequence
<220> FEATURE:
<223> OTHER INFORMATION: Isoform F

<400> SEQUENCE: 6

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
210                 215                 220

Phe Thr Lys Asn Pro Ser Thr Arg Leu Trp Pro Val Leu Glu Thr Asp
225                 230                 235                 240
```

```
Glu Val Val Arg Ser Leu Ile Asp Gly Ile Leu Thr Asn Lys Lys Met
            245                 250                 255

Ile Phe Val Pro Ser Tyr Ile Asn Ile Phe Leu Arg Leu Gln Lys Leu
            260                 265                 270

Ser Thr Ala Gln Asn Thr Gln Ile Leu Lys His Gln
        275                 280

<210> SEQ ID NO 7
<211> LENGTH: 271
<212> TYPE: PRT
<213> ORGANISM: artificial sequence
<220> FEATURE:
<223> OTHER INFORMATION: Isoform F'

<400> SEQUENCE: 7

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
                20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
        50                  55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
        115                 120                 125

Leu Leu Ser Thr Lys Asp Glu Glu Ile Thr Lys Thr Phe Glu Val Asn
    130                 135                 140

Ile Leu Gly His Phe Trp Ile Thr Lys Ala Leu Leu Pro Ser Met Met
145                 150                 155                 160

Glu Arg Asn His Gly His Ile Val Thr Val Ala Ser Val Cys Gly His
                165                 170                 175

Glu Gly Ile Pro Tyr Leu Ile Pro Tyr Cys Ser Ser Lys Phe Ala Ala
            180                 185                 190

Val Gly Phe His Arg Gly Leu Thr Ser Glu Leu Gln Ala Leu Gly Lys
        195                 200                 205

Thr Gly Ile Lys Thr Ser Cys Leu Cys Pro Val Phe Val Asn Thr Gly
    210                 215                 220

Phe Thr Lys Asn Pro Ser Thr Arg Leu Trp Pro Val Leu Glu Thr Asp
225                 230                 235                 240

Glu Val Val Arg Ser Leu Ile Asp Gly Ile Leu Thr Asn Lys Lys Met
                245                 250                 255

Ile Phe Val Pro Ser Tyr Ile Asn Ile Phe Leu Arg Leu Gln Lys
            260                 265                 270

<210> SEQ ID NO 8
<211> LENGTH: 238
<212> TYPE: PRT
<213> ORGANISM: artificial sequence
<220> FEATURE:
<223> OTHER INFORMATION: Isoform G

<400> SEQUENCE: 8
```

```
Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
50                      55                  60

Leu Trp Asp Ile Asn Lys Val Lys Lys Glu Val Gly Asp Val Thr Ile
65                  70                  75                  80

Val Val Asn Asn Ala Gly Thr Val Tyr Pro Ala Asp Leu Leu Ser Thr
                85                  90                  95

Lys Asp Glu Glu Ile Thr Lys Thr Phe Glu Val Asn Ile Leu Gly His
            100                 105                 110

Phe Trp Ile Thr Lys Ala Leu Leu Pro Ser Met Met Glu Arg Asn His
            115                 120                 125

Gly His Ile Val Thr Val Ala Ser Val Cys Gly His Glu Gly Ile Pro
130                 135                 140

Tyr Leu Ile Pro Tyr Cys Ser Ser Lys Phe Ala Ala Val Gly Phe His
145                 150                 155                 160

Arg Gly Leu Thr Ser Glu Leu Gln Ala Leu Gly Lys Thr Gly Ile Lys
                165                 170                 175

Thr Ser Cys Leu Cys Pro Val Phe Val Asn Thr Gly Phe Thr Lys Asn
                180                 185                 190

Pro Ser Thr Arg Leu Trp Pro Val Leu Glu Thr Asp Glu Val Val Arg
                195                 200                 205

Ser Leu Ile Asp Gly Ile Leu Thr Asn Lys Lys Met Ile Phe Val Pro
            210                 215                 220

Ser Tyr Ile Asn Ile Phe Leu Arg Leu Gln Lys Val Ser Ser
225                 230                 235

<210> SEQ ID NO 9
<211> LENGTH: 298
<212> TYPE: PRT
<213> ORGANISM: artificial sequence
<220> FEATURE:
<223> OTHER INFORMATION: Isoform H

<400> SEQUENCE: 9

Met Asn Ile Ile Leu Glu Ile Leu Leu Leu Ile Thr Ile Ile Tyr
1               5                   10                  15

Ser Tyr Leu Glu Ser Leu Val Lys Phe Phe Ile Pro Gln Arg Arg Lys
            20                  25                  30

Ser Val Ala Gly Glu Ile Val Leu Ile Thr Gly Ala Gly His Gly Ile
            35                  40                  45

Gly Arg Gln Thr Thr Tyr Glu Phe Ala Lys Arg Gln Ser Ile Leu Val
50                      55                  60

Leu Trp Asp Ile Asn Lys Arg Gly Val Glu Glu Thr Ala Ala Glu Cys
65                  70                  75                  80

Arg Lys Leu Gly Val Thr Ala His Ala Tyr Val Val Asp Cys Ser Asn
                85                  90                  95

Arg Glu Glu Ile Tyr Arg Ser Leu Asn Gln Val Lys Lys Glu Val Gly
            100                 105                 110

Asp Val Thr Ile Val Val Asn Asn Ala Gly Thr Val Tyr Pro Ala Asp
            115                 120                 125
```

```
Leu Leu Ser Thr Lys Asp Glu Ile Thr Lys Thr Phe Glu Val Asn
    130             135             140
Ile Leu Gly His Phe Trp Asn Gly Lys Asp Ile Arg Ser Asn Tyr Leu
145             150             155             160
Asp Val Tyr Arg Ile Glu Asp Thr Phe Gly Arg Asp Ser Glu Ile Thr
                165             170             175
Lys Ala Leu Leu Pro Ser Met Met Glu Arg Asn His Gly His Ile Val
            180             185             190
Thr Val Ala Ser Val Cys Gly His Glu Gly Ile Pro Tyr Leu Ile Pro
        195             200             205
Tyr Cys Ser Ser Lys Phe Ala Ala Val Gly Phe His Arg Gly Leu Thr
    210             215             220
Ser Glu Leu Gln Ala Leu Gly Lys Thr Gly Ile Lys Thr Ser Cys Leu
225             230             235             240
Cys Pro Val Phe Val Asn Thr Gly Phe Thr Lys Asn Pro Ser Thr Arg
                245             250             255
Leu Trp Pro Val Leu Glu Thr Asp Glu Val Val Arg Ser Leu Ile Asp
            260             265             270
Gly Ile Leu Thr Asn Lys Lys Met Ile Phe Val Pro Ser Tyr Ile Asn
        275             280             285
Ile Phe Leu Arg Leu Gln Lys Val Ser Ser
    290             295
```

ASSAYS FOR SCREENING ACTIVITY OF MODULATORS OF MEMBERS OF THE HYDROXY STEROID (17-BETA) DEHYDROGENASE (HSD17B) FAMILY

CROSS-REFERENCE TO RELATED APPLICATIONS

This claims priority to U.S. Application No. 62/484,141 filed Apr. 11, 2017, which is incorporated herein by reference in its entirety.

REFERENCE TO SEQUENCE LISTING

This application includes a Sequence Listing filed electronically as a text file named 189238001015EQ, created on Feb. 10, 2018, with a size of 22 KB. The Sequence Listing is incorporated herein by reference.

FIELD

This disclosure relates generally to the field of compound screening. More particularly, the disclosure relates to biochemical and cell-based assays in which molecules or compositions are evaluated for their capacity to modulate enzymatic activity of members of the hydroxysteroid (17-beta) dehydrogenase (HSD17B) family, especially their inhibitory capacity.

BACKGROUND

Various publications, including patents, patent applications, published patent applications, accession numbers, technical articles and scholarly articles are cited throughout the specification. Each of these cited publications is incorporated by reference, in its entirety and for all purposes, in this document.

Chronic liver disease and cirrhosis are leading causes of morbidity and mortality in the United States, accounting for 38,170 deaths (1.5% of total deaths) in 2014. The most common etiologies of cirrhosis in the U.S. are alcoholic liver disease, chronic hepatitis C, and nonalcoholic fatty liver disease (NAFLD), together accounting for ~80% of patients awaiting liver transplant between 2004 and 2013. The estimated prevalence of NAFLD in the U.S. is between 19 and 46 and is rising over time, likely in conjunction with increased rates of obesity, its primary risk factor. While significant advances have been made in the treatment of hepatitis C, there are currently no evidence-based treatments for alcoholic or nonalcoholic liver disease and cirrhosis.

SUMMARY

In a first aspect of the disclosure, a method for screening a test compound for capability to modulate one or more members of the hydroxysteroid (17-beta) dehydrogenase (HSD17B) family comprises contacting a first HSD17B family member protein with a test compound, a substrate for the HSD17B family member protein, $NAD^+$ or $NAD(P)^+$, a pre-reduced form of luciferin, an enzyme that reduces the pre-reduced form of luciferin to produce luciferin, and luciferase, contacting a same second HSD17B family member protein with a control, a substrate for the HSD17B family member protein, $NAD^+$ or $NAD(P)^+$, a pre-reduced form of luciferin, an enzyme that reduces the pre-reduced form of luciferin to produce luciferin, and luciferase, detecting the emission wavelength of luciferin produced, and identifying the test compound as an inhibitor of the HSD17B family member protein when the emission wavelength of luciferin produced in the presence of the test compound is lower than the wavelength of luciferin produced in the presence of the control, or identifying the test compound as an activator of the HSD17B family member protein when the emission wavelength of luciferin produced in the presence of the test compound is higher than the wavelength of luciferin produced in the presence of the control.

In a second aspect of the disclosure, a method for screening a test compound for capability to modulate one or more members of the hydroxysteroid (17-beta) dehydrogenase (HSD17B) family comprises contacting a first cell expressing an HSD17B family member protein with a test compound and a substrate for the HSD17B family member protein, contacting a second cell expressing the same HSD17B family member protein with a control and a substrate for the HSD17B family member protein, determining the level of substrate depletion by the cells, and identifying the test compound as an inhibitor of the HSD17B family member protein when the level of substrate depletion in the presence of the test compound is lower than the level of substrate depletion in the presence of the control, or identifying the test compound as an activator of the HSD17B family member protein when the level of substrate depletion in the presence of the test compound is higher than the level of substrate depletion in the presence of the control.

In a third aspect of the disclosure, a method for screening a test compound for capability to modulate one or more members of the hydroxysteroid (17-beta) dehydrogenase (HSD17B) family comprises contacting a first cell expressing an HSD17B family member protein with a test compound and a substrate for the HSD17B family member protein, contacting a second cell expressing the same HSD17B family member protein with a control and a substrate for the HSD17B family member protein, determining the level of substrate product produced by the cells, and identifying the test compound as an inhibitor of the HSD17B family member protein when the level of substrate product produced in the presence of the test compound is lower than the level of substrate product produced in the presence of the control, or identifying the test compound as an activator of the HSD17B family member protein when the level of substrate product produced in the presence of the test compound is lower than the level of substrate product produced in the presence of the control.

In a fourth aspect of the disclosure, a kit for screening a test compound for capability to modulate one or more members of the hydroxysteroid (17-beta) dehydrogenase (HSD17B) family comprises an HSD17B family member protein or a cell expressing an HSD17B family member protein, a substrate for the HSD17B family member protein, and instructions for using the HSD17B family member protein or cell expressing the HSD17B family member protein and substrate in a method for screening a test compound for capability to modulate the HSD17B family member protein. The kit may further comprise a cofactor for the HSD17B family member protein. The cofactor may comprise $NAD^+$ or $NAD(P)^+$.

In a fifth aspect of the disclosure, a complex comprises an HSD17B family member protein and a substrate for the HSD17B family member protein. The complex may further comprise a cofactor for the HSD17B family member protein. The cofactor may comprise $NAD^+$ or $NAD(P)^+$. The complex may be comprised in a composition comprising a carrier, excipient, or both a carrier and excipient.

In a sixth aspect of the disclosure, a composition comprises an HSD17B family member protein, a substrate for the HSD17B family member protein, and a carrier, excipient, or both a carrier and excipient. The composition may further comprise a cofactor for the HSD17B family member protein. The cofactor may comprise NAD$^+$ or NAD(P)$^+$. The composition may further comprise a test compound.

According to any of these aspects, the substrate for the HSD17B family member protein may comprise a steroid hormone or derivative thereof. The steroid hormone may comprise an estrogen hormone such as estradiol (E2) or estrone (E1), or a derivative thereof. The steroid hormone may comprise an androgen hormone such as androstaendiol, testosterone, or dihydroxy testosterone (DHT), or a derivative thereof such as trilostane. According to any of these aspects, the substrate for the HSD17B family member protein may comprise a fatty acid such as ricinoleic acid. According to any of these aspects, the substrate for the HSD17B family member protein may comprise a bioactive lipid, for example, an eicosanoid, including a leukotriene such as leukotriene B4. According to any of these aspects, the HSD17B family member protein preferably comprises a human HSD17B family member protein. According to any of these aspects, the HSD17B family member protein preferably comprises HSD17B13 protein. According to any of these aspects, the HSD17B13 may comprise the amino acid sequence of SEQ ID NO:1, SEQ ID NO:2, SEQ ID NO:3, SEQ ID NO:4, SEQ ID NO:5, SEQ ID NO:6, SEQ ID NO:7, SEQ ID NO:8, or SEQ ID NO:9, or an amino acid sequence that is at least about 90% or at least about 95% or at least about 99% identical thereto.

DETAILED DESCRIPTION

Figure 1:
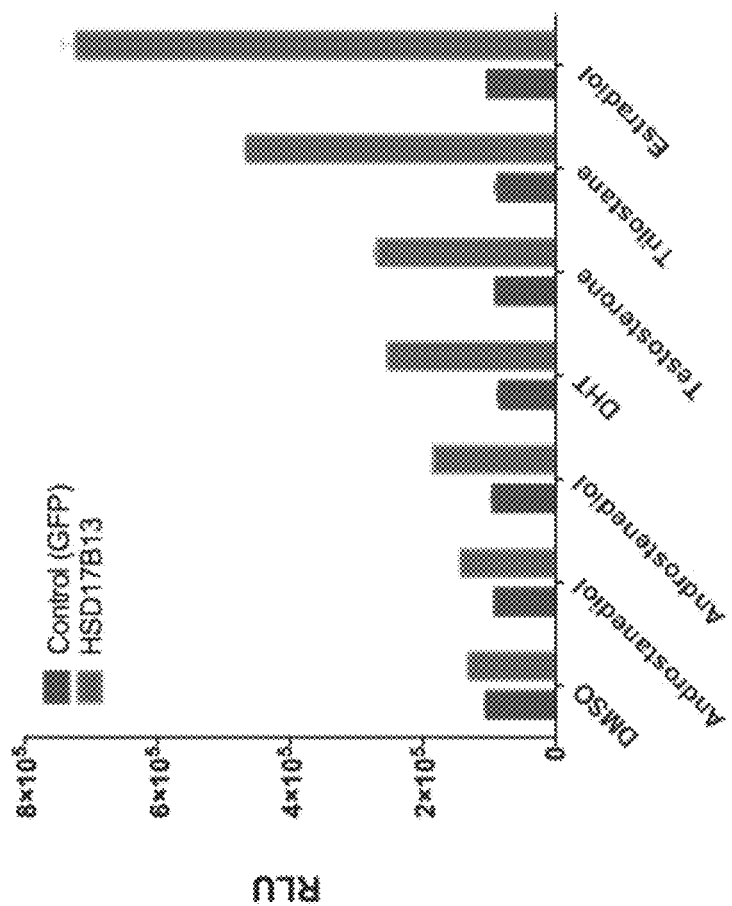
FIG. 1 shows the results of a screen of over 50 steroids with human HSD17B13 using an NADH-linked assay. Steroids and androgens were identified as substrates for HSD17B13. GFP protein was tested in parallel as a control. DMSO served as a substrate control. For each set of bars, the left bar is the GFP control and the right bar is the steroid substrate.

Various terms relating to aspects of disclosure are used throughout the specification and claims. Such terms are to be given their ordinary meaning in the art, unless otherwise indicated. Other specifically defined terms are to be construed in a manner consistent with the definition provided herein.

As used herein, the singular forms "a," "an," and "the" include plural referents unless expressly stated otherwise.

Inhibiting comprises reducing, decreasing, blocking, preventing, delaying, inactivating, desensitizing, stopping, and/or downregulating activity or expression of a molecule or pathway of interest. By way of example, but not of limitation, inhibiting of an HSD17B family member protein, such as HSD17B13, includes inhibiting its enzymatic activity, including the catalysis of chemical reactions of substrates and cofactors such as NAD$^+$ as described or exemplified herein. Inhibiting need not be 100%.

A substrate product includes the product of the chemical reaction of the substrate catalyzed by enzymatic activity.

Determining or detecting may comprise any suitable quantitative or qualitative measurements, according to any suitable technique.

It has been observed in accordance with the disclosure that human hydroxysteroid (17-beta) dehydrogenase 13 (HSD17B13) uses nicotinamide adenine dinucleotide (NAD$^+$) as a cofactor and, accordingly, can be used in an assay for determining HSD17B13 activity. It was further observed that HSD17B13 is highly expressed in liver lipid droplets and catalyzes conversion between keto and hydroxy steroids and lipids. It was further observed that inhibition of HSD17B13 activity in a biochemical assay can be detected. It was also observed that steroids and lipids can serve as substrates for the HSD17B13 enzyme sufficient to measure HSD17B13 activity and inhibition in both biochemical and cell-based inhibitor screening assays. Inhibition of HSD17B13 may have a therapeutic effect in human beings, for example, as a treatment for liver diseases, disorders, or conditions such as one or more of alcoholic liver disease, non-alcoholic liver disease, cirrhosis, and nonalcoholic steatohepatitis (NASH). Accordingly, the disclosure features methods for screening molecules for their capacity to modulate activity of any one or more of the HSD17B family member proteins.

In a first aspect, the disclosure features methods for screening molecules for their capability to modulate one or more HSD17B family member proteins. The screening methods may be according to a biochemical assay or may be according to a cell-based assay. The methods are preferably for screening molecules for their capability to inhibit an HSD17B family member protein. The methods are preferably capable of high throughput. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In some embodiments, a biochemical screening method comprises contacting the HSD17B family member protein with a test compound, a substrate for the HSD17B family member protein, $NAD^+$ or $NAD(P)^+$, a pre-reduced form of luciferin (e.g., form before reduction into luciferin by an enzyme), an enzyme that reduces the pre-reduced form of luciferin to produce luciferin, and luciferase and, in parallel, contacting the same HSD17B family member protein with a control, a substrate for the HSD17B family member protein, $NAD^+$ or $NAD(P)^+$, a pre-reduced form of luciferin, an enzyme that reduces the pre-reduced form of luciferin to produce luciferin, and luciferase. The control is preferably a negative control such that contact with the HSD17B family member protein would not inhibit the HSD17B family member protein. The control may comprise water, any organic or inorganic chemical compound, biomolecule, mixture, or composition thereof that is known not to substantially inhibit the HSD17B family member protein. Following a period of incubation between the test compound or control and assay components, the method further comprises detecting the emission wavelength of luciferin produced by the luciferase. Then, the method comprises comparing the detected emission wavelength of luciferin in both systems— the emission where the test compound and the HSD17B family member protein interacted and the emission where the HSD17B family member protein was in the presence of the control. In some embodiments where the luciferin light emission decreased in the presence of the test compound relative to the light emission in the presence of the control, then the test compound may be identified as an HSD17B family member protein inhibitor. In some embodiments where the luciferin light emission increased in the presence of the test compound relative to the light emission in the presence of the control, then the test compound may be identified as an HSD17B family member protein activator. In some embodiments where the luciferin light emission did not substantially increase or decrease in the presence of the test compound relative to the light emission in the presence of the control, then the test compound may be identified as neither an HSD17B family member protein inhibitor nor an HSDB17 family member protein activator. The biochemical screening method is preferably high throughput. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In some embodiments, a biochemical screening method comprises a scintillation proximity assay (SPA). For example, the method may comprise contacting the HSD17B family member protein with a test compound, an HSD17B family member protein cofactor such as $NAD^+$ or $NAD(P)^+$, and a radio-labeled substrate for the HSD17B family member protein, and, in parallel, contacting the HSD17B family member protein with a control, an HSD17B family member protein cofactor such as $NAD^+$ or $NAD(P)^+$, and a radio-labeled substrate for the HSD17B family member protein. The control is preferably a negative control such that contact with the HSD17B family member protein would not inhibit the HSD17B family member protein. The control may comprise water, any organic or inorganic chemical compound, biomolecule, mixture, or composition thereof that is known not to substantially inhibit the HSD17B family member protein. Following a period of incubation between the test compound or control and assay components, the method further comprises contacting the reaction mixture with an immobilized ligand that captures the radio-labeled substrate such as an antibody that specifically binds to the substrate, and detecting the level of labeled substrate captured by the immobilized ligand. Then, the method comprises comparing the detected level of labeled substrate in both systems—where the test compound and the HSD17B family member protein interacted and where the HSD17B family member protein was in the presence of the control. In some embodiments where the level of labeled substrate decreased in the presence of the test compound relative to the level of labeled substrate in the presence of the control, then the test compound may be identified as an HSD17B family member protein activator. In some embodiments where the level of labeled substrate did not substantially decrease in the presence of the test compound relative to level of labeled substrate in the presence of the control, then the test compound may be identified as an inhibitor of the HSDB17 family member protein. The biochemical screening method is preferably high throughput. As an alternative to a radio-label, the substrate label may comprise a fluorescent label, and detection may be of the fluorescence instead of the scintillation. The label may also be colloidal gold. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

The SPA assay may alternatively be used in accordance with a cell-based screening assay, for example, as described below. In such cases, cells expressing the HSD17B family member protein are used instead of the HSD17B family member protein, and the assay measures the labeled substrate consumed or not consumed by the cells. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

As part of a biochemical assay, the HSD17B family member protein preferably utilizes NAD$^+$ as a cofactor in an enzymatic reaction that catalyzes the chemical reaction converting the substrate of the HSD17B family member protein to its respective substrate product. In this reaction, the HSD17B family member protein catalyzes substrate conversion and catalyzes the reduction of NAD$^+$ to NADH.

In some embodiments, a cell-based screening assay comprises contacting a first cell expressing the HSD17B family member protein with a test compound and a substrate for the HSD17B family member protein and, in parallel, contacting a second cell expressing the same HSD17B family member protein with a control and a substrate for the HSD17B family member protein. The control is preferably a negative control such that contact with the HSD17B family member protein would not inhibit the HSD17B family member protein. The control may comprise water, any organic or inorganic chemical compound, biomolecule, mixture, or composition thereof that is known not to substantially inhibit the HSD17B family member protein. In some embodiments, the method further comprises determining the level of substrate product produced by each of the first cell and the second cell following a period of incubation between the test compound or control and the cells. In some alternative embodiments, the method comprises determining the level of substrate depletion by each of the first cell and the second cell following a period of incubation between the test compound or control and the cells. In some alternative embodiments, the method comprises determining the level of substrate depletion and the level of substrate product produced by each of the first cell and the second cell following a period of incubation between the test compound or control and the cells. Thus, either or both of the level of substrate or substrate product can be detected. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

Then, the method comprises comparing the determined level of substrate depletion, substrate product, or both substrate depletion and substrate product in both systems—the levels where the test compound interacted with the HSD17B family member protein-expressing cells and the levels where the control interacted with the HSD17B family member protein-expressing cells. In some embodiments where the levels of substrate depletion, substrate product, or both substrate depletion and substrate product decreased in the presence of the test compound relative to the respective levels in the presence of the control, then the test compound may be identified as an HSD17B family member protein inhibitor. In some embodiments where the levels of substrate depletion, substrate product, or both substrate depletion and substrate product increased in the presence of the test compound relative to the respective levels in the presence of the control, then the test compound may be identified as an HSD17B family member protein activator. In some embodiments where the levels of substrate depletion, substrate product, or both substrate depletion and substrate product did not substantially increase or decrease in the presence of the test compound relative to the respective levels in the presence of the control, then the test compound may be identified as neither an HSD17B family member protein inhibitor nor an HSDB17 family member protein activator or facilitator. The cell-based method is preferably high throughput. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In cell-based assays, the levels of substrate depletion, substrate product, or both substrate depletion and substrate product may be determined according to any suitable techniques. In some embodiments, the levels are detected using liquid chromatography (LC). In some embodiments, the levels are detected by mass spectrometry (MS). In some embodiments, the levels are detected using both LC and MS (e.g., LC-MS). In some embodiments, the levels are detected using a scintillation proximity assay (SPA), or fluorescence equivalent thereof. In some embodiments, the levels are detected using Homogeneous Time Resolved Fluorescence (HTRF). For example, a labeled substrate and the cell culture medium can be assessed in a competitive immunoassay in which the labeled substrate and the substrate in the cell culture medium compete for binding to an antibody specific for the substrate. HTRF is used to detect the label and allow the concentration of substrate in the cell culture medium to be determined based on the level in which substrate in the cell culture medium out-competed the labeled substrate in the assay.

The cells of the methods and kits, which cells are used to express the HSD17B family member protein, may be any cell capable of expressing the HSD17B family member protein. In some embodiments, the cells may be primary isolates, e.g., liver cells in which the HSD17B family member protein is expressed. In some embodiments, the cells of the methods and kits are liver cells. In some embodiments, the cells of the methods and kits are not brain cells. In some embodiments, the HSD17B family member protein is expressed primarily in liver cells and not primarily in brain cells. In some embodiments, at least 50% of the HSD17B family member protein expressed in the body is expressed in liver cells. In some embodiments, at least 60% of the HSD17B family member protein expressed in the body is expressed in liver cells. In some embodiments, at least 70% of the HSD17B family member protein expressed in the body is expressed in liver cells. In some embodiments, at least 80% of the HSD17B family member protein expressed in the body is expressed in liver cells. In some embodiments, at least 90% of the HSD17B family member protein expressed in the body is expressed in liver cells.

In some embodiments, the primary isolate cells can be obtained from a biopsy specimen. In preferred embodiments, the cells are recombinant cells such as mammalian cells, bacterial cells, yeast cells, or insect cells; mammalian cells are preferred. The cells may be transfected with a gene encoding the HSD17B family member protein or variant or isoform thereof, and expression of this gene may be constitutive or under regulatory control, e.g., inducible expression. The transfection vector may be a plasmid, virus, or any other suitable vector. In some preferred embodiments, the cells are HEK293 cells. It is preferred that the first and second cells are the same. By way of example but not of limitation, where HEK293 cells are used in the assay, both the first cell and the second cell are HEK293 cells expressing an HSD17B family member protein, such as, for example, HSD17B13. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

Test compounds used in any of the methods may be any molecule, chemical, biomolecule, or mixture of composition thereof. Chemicals may comprise any organic or inorganic compound. Biomolecules may comprise any nucleic acid, monosaccharide, polysaccharide, fatty acid, lipid, polypeptide, protein, or combination or fragment or derivative thereof. A composition may include any carrier or excipient.

In another aspect, the disclosure features kits for screening molecules for their capability to modulate one or more HSD17B family member proteins. The kits may be used in biochemical screening assays. The kits may be used in cell-based screening assays. The kits are preferably used to carry out biochemical or cell-based methods for screening molecules for their capability to inhibit the HSD17B family member protein. The kits preferably are used for screening molecules for their capability to inhibit the HSD17B family member protein. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In some embodiments, the kits comprise an HSD17B family member protein, a substrate for the HSD17B family member protein, and instructions for using the HSD17B family member protein and substrate in a method for screening a test compound for capability to modulate and, preferably inhibit, the HSD17B family member protein. The kit may further comprise one or more of NAD$^+$, NAD(P)$^+$, NADH, NAD(P)H, a pre-reduced form of luciferin, an enzyme that reduces the pre-reduced form of luciferin to produce luciferin, and luciferase. The kit may further comprise a support, for example, a plate comprising a plurality of wells to facilitate the screening assay. The kit may further comprise a negative control (e.g., that which does not inhibit the capability of the HSD17B family member protein to catalyze the conversion of the substrate to a substrate product). The control may comprise water, any organic or inorganic chemical compound, biomolecule, mixture, or composition thereof that is known not to substantially inhibit the HSD17B family member protein. The kit may further comprise a positive control (e.g., that which is a known inhibitor of the capability of the HSD17B family member protein to catalyze the conversion of the substrate to a substrate product). The positive control inhibitor of the HSD17B family member protein may comprise equilin. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In some embodiments, the kits comprise a cell capable of expressing an HSD17B family member protein, a substrate for the HSD17B family member protein, and instructions for using the HSD17B family member protein (e.g., using the cell expressing the HSD17B family member protein) and substrate in a method for screening a test compound for capability to modulate and, preferably inhibit, the HSD17B family member protein. In some alternative embodiments, the kits comprise competent cells and a gene or vector encoding the HSD17B family member protein, as well as instructions to transfect the cells with the gene or vector in order that the cells may express the HSD147B family member protein. The kit may further comprise a support, for example, a plate comprising a plurality of wells to facilitate cell culture and/or the screening assay. The kit may further comprise cell culture media. The kit may further comprise a negative control (e.g., that which does not inhibit the capability of the HSD17B family member protein to catalyze the conversion of the substrate to a substrate product). The control may comprise water, any organic or inorganic chemical compound, biomolecule, mixture, or composition thereof that is known not to substantially inhibit the HSD17B family member protein. The kit may further comprise a positive control (e.g., that which is a known inhibitor of the capability of the HSD17B family member protein to catalyze the conversion of the substrate to a substrate product). The positive control inhibitor of the HSD17B family member protein may comprise equilin. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In another aspect, the disclosure provides HSD17B family member protein complexes. In some embodiments, the complex comprises an HSD17B family member protein and NAD$^+$ or NAD(P)$^+$. In some embodiments, the complex of an HSD17B family member protein and NAD$^+$ or NAD(P)$^+$ further comprises a substrate of the HSD17B family member protein. In some embodiments, the complex of an HSD17B family member protein and NAD$^+$ or NAD(P)$^+$ further comprises a test compound. Any such complexes may be comprised in a composition. The composition may comprise any suitable carrier or excipient. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In another aspect, the disclosure provides compositions comprising one or more HSD17B family member proteins. In some embodiments, the composition comprises an HSD17B family member protein, NAD$^+$ or NAD(P)$^+$, and a carrier. In some embodiments, the composition of an HSD17B family member protein, NAD$^+$ or NAD(P)$^+$, and a carrier further comprises a substrate of the HSD17B family member protein. In some embodiments, the composition of an HSD17B family member protein, NAD$^+$ or NAD(P)$^+$, and a carrier further comprises a test compound. In some embodiments, the composition of an HSD17B family member protein, NAD$^+$ or NAD(P)$^+$, carrier, and a substrate for an HSD17B family member protein further comprises a test compound. The composition may comprise any suitable carrier or excipient. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In any of the biochemical assays, cell-based assays, compositions, complexes, or kits described or exemplified herein, the HSD17B family member protein may comprise a full-length or active/functional fragment of the HSD17B family member protein. The HSD17B family member protein may comprise a variant or isoform of the wildtype HSD17B family member protein. The HSD17B family member protein, or variants and isoforms thereof, may include any HSD17B family member protein, fragment, or isoform thereof. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

The HSD17B family member protein, or variants and isoforms thereof, may include any HSD17B13 protein, fragment, or isoform thereof described in, for example, PCT Application No. PCT/US18/14357. HSD17B13 protein isoforms include, but are not limited to, Isoform A (the wild type), Isoform B, Isoform C, Isoform D, Isoform E, Isoform F, Isoform F', Isoform G, and Isoform H. The HSD17B13 protein may comprise an amino acid sequence at least about 90%, at least about 95%, at least about 96%, at least about 97%, at least about 98%, at least about 99%, or 100% identical to HSD17B13 Isoform A, B, C, D, E, F, F', G, or H when optimally aligned with Isoform A, B, C, D, E, F, F', G, or H, respectively. In preferred embodiments, the active variant of HSD17B13 does not comprise the Y185A alteration at the catalytic site.

HSD17B13 Isoform A comprises the amino acid sequence:
(SEQ ID NO: 1)
MNIILEILLLLITIIYSYLESLVKFFIPQRRKSVAGEIVLITGAGHGI

GRCITTYEFAKRQSILVLWDINKRGVEETAAECRKLGVTAHAYVVDCS

NREEIYRSLNQVKKEVGDVTIVVNNAGTVYPADLLSTKDEEITKTFEV

NILGHFWITKALLPSMMERNHGHIVTVASVCGHEGIPYLIPYCSSKFA

AVGFHRGLTSELQALGKTGIKTSCLCPVFVNTGFTKNPSTRLWPVLET

DEVVRSLIDGILTNKKMIFVPSYINIFLRLQKFLPERASAILNRMQNI

QFEAVVGHKIKMK.

HSD17B13 Isoform B comprises the amino acid sequence:
(SEQ ID NO: 2)
MNIILEILLLLITIIYSYLESLVKFFIPQRRKSVAGEIVLITGAGHGI

GRCITTYEFAKRQSILVLWDINKVKKEVGDVTIVVNNAGTVYPADLLS

TKDEEITKTFEVNILGHFWITKALLPSMMERNHGHIVTVASVCGHEGI

PYLIPYCSSKFAAVGFHRGLTSELQALGKTGIKTSCLCPVFVNTGFTK

NPSTRLWPVLETDEVVRSLIDGILTNKKMIFVPSYINIFLRLQKFLPE

RASAILNRMQNIQFEAVVGHKIKMK.

HSD17B13 Isoform C comprises the amino acid sequence:
(SEQ ID NO: 3)
MNIILEILLLLITIIYSYLESLVKFFIPQRRKSVAGEIVLITGAGHGI

GRCITTYEFAKRQSILVLWDINKRGVEETAAECRKLGVTAHAYVVDCS

NREEIYRSLNQVKKEVGDVTIVVNNAGTVYPADLLSTKDEEITKTFEV

NILGHFWITKALLPSMMERNHGHIVTVASVCGHEGIPYLIPYCSSKFA

AVGFHRGLTSELQALGKTGIKTSCLCPVFVNTGFTKNPSTRFLPERAS

AILNRMQNIQFEAVVGHKIKMK.

HSD17B13 Isoform D comprises the amino acid sequence:
(SEQ ID NO: 4)
MNIILEILLLLITIIYSYLESLVKFFIPQRRKSVAGEIVLITGAGHGI

GRCITTYEFAKRQSILVLWDINKRGVEETAAECRKLGVTAHAYVVDCS

NREEIYRSLNQVKKEVGDVTIVVNNAGTVYPADLLSTKDEEITKTFEV

NILGHFWITKALLPSMMERNHGHIVTVASVCGHEGIPYLIPYCSSKFA

AVGFHRGLTSELQALGKTGIKTSCLCPVFVNTGFTKNPSTRLWPVLET

DEVVRSLIDGILTNKKMIFVPSYINIFLRLQKVSS.

HSD17B13 Isoform E comprises the amino acid sequence:
(SEQ ID NO: 5)
MNIILEILLLLITIIYSYLESLVKFFIPQRRKSVAGEIVLITGAGHGI

GRCITTYEFAKRQSILVLWDINKRGVEETAAECRKLGVTAHAYVVDCS

NREEIYRSLNQVKKEVGDVTIVVNNAGTVYPADLLSTKDEEITKTFEV

NILGHFWNGKDIRSNYLDVYRIEDTFGRDSEITKALLPSMMERNHGHI

VTVASVCGHEGIPYLIPYCSSKFAAVGFHRGLTSELQALGKTGIKTSC

LCPVFVNTGFTKNPSTRLWPVLETDEVVRSLIDGILTNKKMIFVPSYI

NIFLRLQKFLPERASAILNRMQNIQFEAVVGHKIKMK.

HSD17B13 Isoform F comprises the amino acid sequence:
(SEQ ID NO: 6)
MNIILEILLLLITIIYSYLESLVKFFIPQRRKSVAGEIVLITGAGHGI

GRCITTYEFAKRQSILVLWDINKRGVEETAAECRKLGVTAHAYVVDCS

NREEIYRSLNQVKKEVGDVTIVVNNAGTVYPADLLSTKDEEITKTFEV

-continued

NILGHFWITKALLPSMMERNHGHIVTVASVCGHEGIPYLIPYCSSKFA

AVGFHRGLTSELQALGKTGIKTSCLCPVFVNTGFTKNPSTRLWPVLET

DEVVRSLIDGILTNKKMIFVPSYINIFLRLQKLSTAQNTQILKHQ.

HSD17B13 Isoform F' comprises the amino acid
sequence:
(SEQ ID NO: 7)
MNIILEILLLLITIIYSYLESLVKFFIPQRRKSVAGEIVLITGAGHGI

GRCITTYEFAKRQSILVLWDINKRGVEETAAECRKLGVTAHAYVVDCS

NREEIYRSLNQVKKEVGDVTIVVNNAGTVYPADLLSTKDEEITKTFEV

NILGHFWITKALLPSMMERNHGHIVTVASVCGHEGIPYLIPYCSSKFA

AVGFHRGLTSELQALGKTGIKTSCLCPVFVNTGFTKNPSTRLWPVLET

DEVVRSLIDGILTNKKMIFVPSYINIFLRLQK.

HSD17B13 Isoform G comprises the amino acid
sequence:
(SEQ ID NO: 8)
MNIILEILLLLITIIYSYLESLVKFFIPQRRKSVAGEIVLITGAGHGI

GRCITTYEFAKRQSILVLWDINKVKKEVGDVTIVVNNAGTVYPADLLS

TKDEEITKTFEVNILGHFWITKALLPSMMERNHGHIVTVASVCGHEGI

PYLIPYCSSKFAAVGFHRGLTSELQALGKTGIKTSCLCPVFVNTGFTK

NPSTRLWPVLETDEVVRSLIDGILTNKKMIFVPSYINIFLRLQKVSS.

HSD17B13 Isoform H comprises the amino acid
sequence:
(SEQ ID NO: 9)
MNIILEILLLLITIIYSYLESLVKFFIPQRRKSVAGEIVLITGAGHGI

GRCITTYEFAKRQSILVLWDINKRGVEETAAECRKLGVTAHAYVVDCS

NREEIYRSLNQVKKEVGDVTIVVNNAGTVYPADLLSTKDEEITKTFEV

NILGHFWNGKDIRSNYLDVYRIEDTFGRDSEITKALLPSMMERNHGHI

VTVASVCGHEGIPYLIPYCSSKFAAVGFHRGLTSELQALGKTGIKTSC

LCPVFVNTGFTKNPSTRLWPVLETDEVVRSLIDGILTNKKMIFVPSYI

NIFLRLQKVSS.

In any of the biochemical assays, cell-based assays, compositions, complexes, or kits described or exemplified herein, the substrate for the HSD17B family member protein may comprise any suitable substrate whose conversion to a product is catalyzed by an HSD17B family member protein activity. In some embodiments, the substrate for the HSD17B family member protein comprises a steroid hormone, or a steroid hormone derivative. In some embodiments, the substrate for the HSD17B family member protein comprises a nuclear hormone, or a nuclear hormone derivative. In some embodiments, the substrate for the HSD17B family member protein comprises a bioactive lipid, or a bioactive lipid derivative. In some embodiments, the substrate for the HSD17B family member protein comprises a fatty acid, or a fatty acid derivative. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

The steroid hormone may comprise a panel or any one or more of the following: DHT; androstenedione; estrone; beta-estradiol; dehydroepiandrosterone; progesterone; testosterone; androsterone; 6-ethylchenodeoxycholic acid; 5a-androstanedione; androstenediol; androstanediol; CP2308; CP2309; CP2310; CP2311; CP2299; formestane; (2a,3a,5a,17b)-androstan-17-o1,2,3-epithio-17-methyl; epiandrosterone; superdrol; 3b,5-dihydroxy-6b,7b:15b,16b-dimethylene-5b-androstan17-one; oxymetholone; (2b,3a,5a, 16b,17b)-2-(4-morpholinyl)-16-(1-pyrrolidinyl)androstane-3,17-diol; 5-alpha-androstane-3-beta,17-beta-diol; androstanolone 17-benzoate; dromostanolone proprionate; epiandrosterone acetate; androstanolone acetate; stanazol; rostafuroxin; 5-alpha-androsta-2,16-dien-17-yl acetate; 5-alpha-dihydrocortisol; pregnanetriol; 2-alpha,3-alpha, 5-alpha,16-beta,17-beta-16-(1-pyrrolidinyl)-2.3-epoxyandrosterone; 11-oxo-androsterone; 2-alpha,3-alpha,5-alpha,16-beta-16-(1-pyrrolidinyl)-2.3-epoxyandrosterone; 16-alpha-hydroxyandrosterone; cortisone 21-acetate; corticosterone 21-acetate; 5-alpha-tetrahydrocortisol; 5-alpha-androstane-3,11,17-trione; 11-beta-hydroxyandrosterone; corticosterone; cortisol; prednisone; and cortisone.

The nuclear hormone may comprise a panel or any one or more of the following: 25-hydroxyvitamin D3; retinoic acid, all trans.; 9-cis retinoic acid; 13-cis retinoic acid; 4-Hydroxyphenylretinamide; AM-580; TTNPB; methoprene acid; WY-14643; ciglitazone; tetradecylthioacetic acid; 5,8, 11,14-eicosatetraynoic acid; 6-formylindolo [3,2-B] carbazole; diindolylmethane; acetyl-S-farnesyl-L-cysteine; S-farnesyl-L-cysteine methyl ester; n-acetyl-S-geranygeranyl-L-cysteine; AGC (acetyl-geranyl-cysteine); farnesylthioacetic acid; bezafibrate; LY 171883; 15-deoxy-D12,14-prostaglandin J2; troglitazone; CITCO; paxilline; 24(S)-hydroxycholesterol; 24(S),25-epoxycholesterol; pregnenolone-16(alpha)-carbonitrile; clofibric acid; BADGE; GW9662; gemfibrozil; GW7647; 3,5-diiodo-L-thyronine; 3,5-diiodo-L-tyrosine; 13-cis-retinol; retinyl acetate; 3,5-diiodo-4-hydroxyphenylpropionic acid; cholic acid; deoxycholic acid; chenodeoxycholic acid; glycocholic acid; glycodeoxycholic acid; taurocholic acid; taurodeoxycholic acid; rifampicin; dexamethasone; lithocholic acid; 5b-pregnan-3,20-dione; adapalene; farnesol; 3a,5a-androstenol; 3a,5a-androstanol; z-guggulsterone; TCPOBOP; N-oleoylethanolamide; GW4064; geranylgeraniol; 6a-fluorotestosterone; tamoxifen; mifepristone; estrone; 3(S)-hydroxy-9Z,11E-octadecadienoic acid; cortisone; progesterone; 17b-estradiol; pregnenolone; androstenedione; la,25-dihydroxyvitamin D3; cosa-4Z,7Z,10Z,13Z,16Z,19Z-hexaenoic acid; 3-methylcholanthrene; acitretin; pioglitazone; and 4-hydroxyretinoic acid.

The bioactive lipid may comprise a panel or any one or more of the following: 5(S)-HETE; (±)5-HETE; 8(S)-HETE; 9(S)-HETE; 12(S)-HETE; 15(S)-HETE; 15(S)-HEDE; CAY10514; tetranor-12(R)-HETE; 15(S)-HETrE; (±)5-HEPE; 5(S)-HPETE; 12(S)-HPETE; 15(S)-HPETE; 15(5)-HPEDE; 15(S)-HPEPE; (±)4-hydroxynon-2-enal; hepoxilin $A_3$; hepoxilin $B_3$; 12(S),20-DIHETE; 5(S),15(S)-DIHETE; 8(S),15(S)-DIHETE; 5(S),6(R)-DIHETE; 5(S),12(R)-DIHETE all trans; 8(R),15(S)-DIHETE all trans; 5(5), 12(5)-DIHETE all trans; 8(5),15(5)-DIHETE all trans; 5,6-epoxyeicosatrienoic acid; 8,9-epoxyeicosatrienoic acid; 11,12-epoxyeicosatrienoic acid; 14,15-epoxyeicosatrienoic acid; 5-ketoeicosatetraenoic acid; 15-ketoeicosatetraenoic acid; 13-ketooctadecadienoioc acid; leukotriene $B_3$; leukotriene $B_4$; 20-hydroxy-leukotriene $B_4$; leukotriene $C_4$; leukotriene $D_4$; leukotriene $E_4$; n-acetyl-leukotriene $E_4$; prostaglandin $A_1$; prostaglandin $A_2$; prostaglandin $B_1$;

prostaglandin B$_2$; prostaglandin E$_1$; prostaglandin E$_2$; prostaglandin F$_{2a}$; prostaglandin F$_{1a}$; prostaglandin I$_2$ Na; 15-keto-prostaglandin E$_2$; 15-keto-prostaglandin F$_{2a}$; 14-dihydro-keto-prostaglandin F; 6-keto-prostaglandin F$_{1a}$; 16,16-dimethyl-prostaglandin E$_2$; U-46619; 9b,11a Prostaglandin F$_2$; 9a,11b Prostaglandin F$_2$; Prostaglandin J$_2$; 2,3-dinor-6-keto-prostaglandin F$_{1a}$; carbacyclin; (±)13-azaprostanoic acid; 19(R)-hydroxy-prostaglandin E$_2$; 19(R)-hydroxy-prostaglandin F$_{2a}$; 17-phenyl-trinor-prostaglanding E$_2$; D12-prostaglandin J$_2$; 13,14-dihydro-prostaglandin E$_1$; 8-epi-prostaglandin F$_{2a}$; 15d-prostaglandin J$_2$; misoprostol, free acid; thromboxane B$_2$; anandamide (20:4, n-6); palmitylethanolamide; anandamide (18:2, n-6); anandamide (20: 3, n-6); anandamide (22:4, n-6); Mead ethanolamide; (R)-methandamide; BML-190; N-arachidonylglycine; WIN 55,212-2; arachidonamide; linoleamide; 9,10-Octadecenoamide; acetyl-farnesyl-cysteine; S-farnesyl-L-cysteine methylester; AGGC; AGC; farnesylthioacetic acid; 9(S)-HODE; (±)9-HODE; 13(S)-HODE; (±)13-HODE; 13(S)-HOTE; 9(S)-HPODE, 13(S)-HPODE; PACOCF3; leukotoxin B (12,13-EODE); 12(S)-HHT; 25-dihydroxyvitamin D$_3$; 1,25-dihydroxyvitamin D$_3$; 24(R),25-dihydroxyvitamin D$_3$; retinoic acid, all trans; 9-cis retinoic acid; 13-cis retinoic acid; 4-hydroxyphenylretinamide; AM-580; TTNPB; methoprene acid; WY-14643; ciglitazone; clofibrate; 5,8,11-eicosatriynoic acid; 5,8,11,14-eicosatetraynoic acid; 1,2-didecanoyl-glycerol (10:0); 1,2-dioctanoyl-SN-glycerol; 1,2-dioleoyl-glycerol (18:1); 1-Oleoyl-2-acetyl-glycerol; 1-stearoyl-2-arachidonoyl-glycerol; ricinoleic acid; AACOCF3; 1-hexadecyl-2-O-methyl-glycerol; 1-hexadecyl-2-O-acetyl-glycerol; rosmarinic acid; 14,15-dehydro-leukotriene B$_4$; REV-5901; LY-171883; U-75302; SQ-29548; fluprostenol; cloprostenol·Na; eicosapentaenoic acid (20:5, n-3); docosahexaenoic acid (22:6, n-3); arachidonic acid (20:4, n-6); Mead acid (20:3, n-9); linolenic acid (18:3, n-3); gamma-linolenic acid (18:3, n-6); eicosa-5,8-dienoic acid (20:2, n-12); eicosadienoic acid (20:2, n-6); 7,7-dimethyleicosadienoic acid; eicosatrienoic acid (20:3, n-3); dihomo-gamma-linolenic acid; docosatrienoic acid (22:3, n-3); adrenic acid (22:4, n-6); docosapentaenoic acid; linoleic acid; 17-Octadecynoic acid; 2-hydroxymyristic acid; 2-fluoropalmitic acid; 4-Oxatetradecanoic acid; 12-methoxydodecanoic acid; sphingosine; C2 ceramide; C2 dihydroceramide; N,N-dimethylsphingosine; C8 ceramide; C8 dihydroceramide; C16 ceramide; dihydrosphingosine; C8 ceramine; DL-dihydrosphingosine; DL-PDMP; DL-PPMP; D-erythro MAPP; L-erythro MAPP; PAF C16; LYSO-PAF C16; PAF C18; PAF C18:1; enantio-PAF C16; arachidonyl-PAF; 2-EPA-PAF; 2-DHLA-PAF; DCHA-PAF; 1-hexadecyl-2-methylglycero-3 PC; 1-octadecyl-2-methylglycero-3 PC; C-PAF; 1-acyl-PAF; lysophosphatidic acid; L-NASPA; dipalmitoylphosphatidic acid; AM251; 2-arachidonoylglycerol; formylindolo [3,2-B] carbazole; diindolylmethane; N-linoleoylglycine; palmitoyl dopamine; oleoyl dopamine; and arachidonyl dopamine.

The fatty acid may comprise a panel or any one or more of the following: decanoic acid; undecanoic acid; 10-undecenoic acid; dodecanoic acid; 11-dodecenoic acid; tridecanoic acid; 12-methoxydodecanoic acid; 12-tridecenoic acid; tetradecanoic acid; 9(Z)-tetradecenoic acid; 9(E)-tetradecenoic acid; pentadecanoic acid; 10(Z)-pentadecenoic acid; 10(E)-pentadecenoic acid; hexadecanoic acid; 9(Z)-hexadecenoic acid; 9(E)-hexadecenoic acid; heptadecanoic acid; 10(Z)-heptadecenoic acid; 10(E)-heptadecenoic acid; octadecanoic acid; 6(Z)-octadecenoic acid; 6(E)-octadecenoic acid; 9(Z)-octadecenoic acid; 9(E)-octadecenoic acid; 11(Z)-octadecenoic acid; 11(E)-octadecenoic acid; 9(Z),11 (Z)-octadecadienoic acid; (9Z,11E)-octadecadienoic acid; 9(E),12(E)-octadecadienoic acid; 9(Z),12(Z),15(Z)-octadecatrienoic acid; 6(Z),9(Z),12(Z)-octadecatrienoic acid; nonadecanoic acid; 7(Z)-nonadecenoic acid; 7(E)-nonadecenoic acid; 10(Z)-nonadecenoic acid; 10(E)-nonadecenoic acid; 10(Z),13(Z)-nonadecadienoic acid; 6(Z),9(Z),12(Z),15 (Z)-octadecatetraenoic acid; eicosanoic acid; 11(E)-eicosenoic acid; 8(Z)-eicosenoic acid; 11(Z)-eicosenoic acid; 5(Z)-eicosenoic acid; 5(Z),8(Z)-eicosadienoic acid; 5(Z),8(Z)-7dimethyleicosadienoic acid; 11(Z),14(Z)-eicosadienoic acid; 5(Z),8(Z),11(Z)-eicosatrienoic acid; 5(Z),11(Z),14(Z)-eicosatrienoic acid; 11(Z),14(Z),17(Z)-eicosatrienoic acid; 5(Z),8(Z),11(Z),14(Z)-eicosatetraenoic acid; 5(Z),8(Z),11 (Z),14(Z),17(Z)-eicosapentaenoic acid; heneicosanoic acid; 12(Z) heneicosenoic acid; 13(Z)-docosenoic acid; 13(E)-docosenoic acid; 13(Z),16(Z),19(Z)-docosatrienoic acid; 7(Z),10(Z),13(Z),16(Z)-ocosatetraenoic acid; 7(Z),10(Z),13 (Z),16(Z),19(Z)-docosapentaenoic acid; 4(Z),7(Z),10(Z),13 (Z),16(Z),19(Z)-docosahexaenoic acid; 14(Z)-tricosenoic acid; 14(E)-tricosenoic acid; tetracosanoic acid; and 15(Z)-tetracosenoic acid.

In some preferred embodiments, the substrate for the HSD17B family member protein comprises an estrogen hormone. The estrogen hormone may comprise estradiol (E2). The estrogen hormone may comprise estrone (E1). It is believed that in a cell-free system, the HSD17B family member protein enzyme may convert E2 to E1 in the presence of NAD$^+$ as a cofactor, but also may convert E1 to E2 in the presence of NADH as a cofactor. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In some preferred embodiments, the substrate for the HSD17B family member protein comprises an androgen hormone. The androgen hormone may comprise androstaendiol. The androgen hormone may comprise testosterone. The androgen hormone may comprise dihydroxy testosterone (DHT). In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In some preferred embodiments, the substrate for the HSD17B family member protein comprises an androgen hormone derivative. The androgen hormone derivative may comprise trilostane. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In some preferred embodiments, the substrate for the HSD17B family member protein comprises a fatty acid. The fatty acid may comprise ricinoleic acid. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In some preferred embodiments, the substrate for the HSD17B family member protein comprises a bioactive lipid. In some preferred embodiments, the bioactive lipid comprises an eicosanoid. The eicosanoid may comprise a leukotriene. The leukotriene may comprise leukotriene B4. In some embodiments, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14. In some embodiments, the HSD17B family member protein is one or more of HSD17B1, HSD17B2, HSD17B4, HSD17B5, HSD17B10, HSD17B11, or HSD17B13. In some embodiments, the HSD17B family member protein is HSD17B13.

In any of the embodiments described herein, the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14, or any combination thereof. In some embodiments, the HSD17B family member protein is one or more of HSD17B1, HSD17B2, HSD17B4, HSD17B5, HSD17B10, HSD17B11, or HSD17B13, or any combination thereof. In some embodiments, the HSD17B family member protein is HSD17B1. In some embodiments, the HSD17B family member protein is HSD17B2. In some embodiments, the HSD17B family member protein is HSD17B3. In some embodiments, the HSD17B family member protein is HSD17B4. In some embodiments, the HSD17B family member protein is HSD17B5. In some embodiments, the HSD17B family member protein is HSD17B6. In some embodiments, the HSD17B family member protein is HSD17B7. In some embodiments, the HSD17B family member protein is HSD17B8. In some embodiments, the HSD17B family member protein is HSD17B9. In some embodiments, the HSD17B family member protein is HSD17B10. In some embodiments, the HSD17B family member protein is HSD17B11. In some embodiments, the HSD17B family member protein is HSD17B12. In some embodiments, the HSD17B family member protein is HSD17B13. In some embodiments, the HSD17B family member protein is HSD17B14.

Percent identity (or percent complementarity) between particular stretches of amino acid sequences within polypeptides can be determined routinely using BLAST programs (basic local alignment search tools) and PowerBLAST programs (Altschul et al., J. Mol. Biol., 1990, 215, 403-410; Zhang and Madden, Genome Res., 1997, 7, 649-656) or by using the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482-489). Herein, if reference is made to percent sequence identity, the higher percentages of sequence identity are preferred over the lower ones.

EXAMPLES

The following examples are provided to describe the disclosure in greater detail. They are intended to illustrate, not to limit, the disclosure.

Example 1: Human HSD17B13 Utilizes Estrogens and Androgens as Substrates

Compound libraries were screened as substrates for HSD17B13. The compound libraries included a steroid panel (described above), a nuclear hormone receptor panel (described above) (Enzo, cat. #BML-2802-0100), a bioactive lipid panel (described above) (Enzo, cat. #BML-2800-0100), and a fatty acid panel (described above) (Enzo, cat. #BML-2803-0100).

A biochemical assay was employed to screen the compounds from the library. The assay employed the following reaction conditions: 0.1 M Potassium phosphate buffer pH 7.5, 0.5 mM NAD$^+$, 50 µM substrate in DMSO 2% reaction volume or DMSO alone (no substrate) as a control, and 1 µl of purified enzyme or green fluorescent protein (GFP) as a control, with a final reaction volume of 100 microliters. Test samples were subject to a 24 hr incubation at 25 degrees C. After incubation, 20 µL reaction above+20 µL luciferase were incubated at room temperature for 1 h and read on an Envision Plate Reader (Perkin Elmer). The results are shown in FIG. 1. The results showed that estrogens, especially estradiol (E2), and androgens and androgen derivatives such as trilostane are suitable substrates for HSD17B13.

A cell-based assay was employed to screen the compounds from the library. The biochemical results from a HEK293 cell based assay was applied to calculate the consumption of substrate candidates and the conversion of the expected products.

HEK293 cells overexpressing HSD17B13 isoform A or green fluorescent protein (GFP) were plated into a 24 well plate (1×10$^5$ cells with 500 µL of culture medium/well). Estradiol or androstanediol was added at 1 µM. After 2 hours or 48 hours of incubation, 40 µL of culture medium was transferred from each well into a 96 well plate.

The proteins were removed by adding 200 µL of methanol to each sample followed by incubation at 20 degrees C. for 20 min and centrifugation at 900×g for 10 minutes. One hundred µL of supernatant containing estradiol or androstanediol was transferred to a new plate for LC-MS analysis. A calibration curve for each compound was established over the concentration range 1 µM to 3.9 nM (1:2 serial dilution).

The consumption of estradiol and androstanediol was evaluated by LC-MS using a Thermo Q Exactive™ HF mass spectrometer with a Waters I class ACQUITY UPLC system. Ten pi of each sample was loaded onto a pre-equilibrated Acquity UPLC BEH C18 column (2.1 mm×15 cm, particle size 1.7 µM). The flow rate was 0.3 mL/min (Mobile Phase A: water:formic acid/100:0.1 [V:V] and Mobile Phase B: acetonitrile:formic acid/100:0.1 [V:V]).

Figure 2:
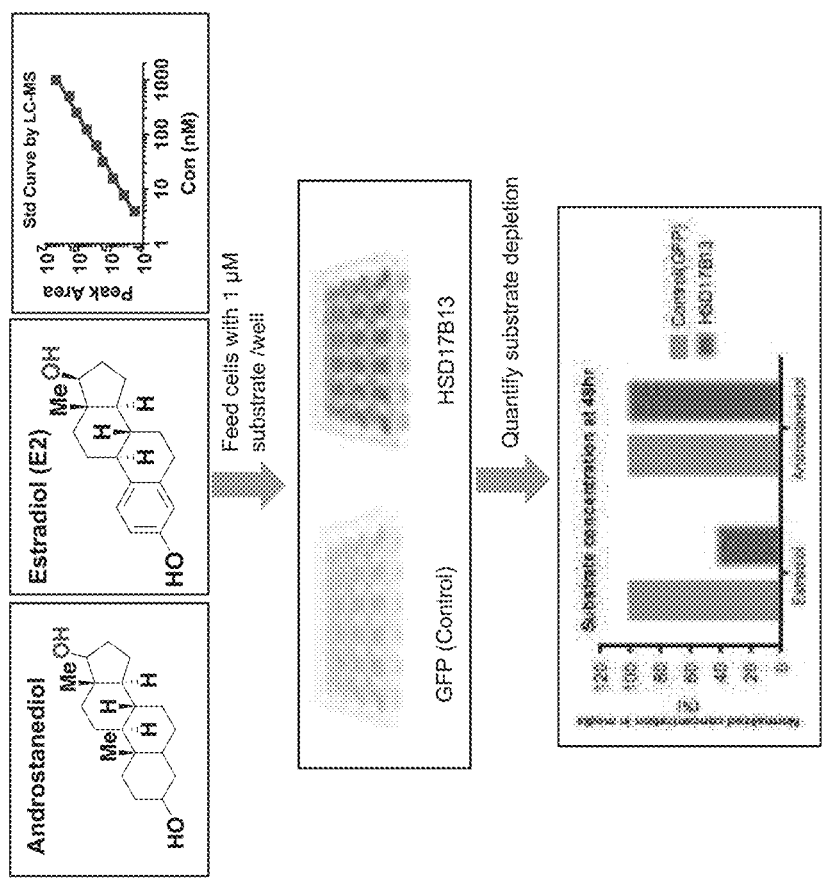
FIG. 2 shows confirmation that estradiol is a substrate for HSD17B13 in a cell-based assay. HEK 293 cells expressing HSD17B3 or GFP as a control were cultured in the presence of substrate (androstanediol or estradiol), with the substrate depletion measured by LC-MS. The results are plotted in the lower panel. For each set of bars, the left bar is the GFP control and the right bar is the steroid substrate.

Retention time and peak area of all compounds were determined using Xcalibur™ software. The concentration of each compound was calculated from the calibration curves, which were constructed by plotting the peak area of each compound versus corresponding concentration. The results are shown in FIG. 2. In the bottom panel of FIG. 2, it is shown that HSD17B13 catalyzed the conversion of estradiol, but did not substantially catalyze the conversion of androstanediol in the cell-based assay.

Example 2: Human HSD17B13 Utilizes Leukotriene B4 as Substrates

Figure 3A:
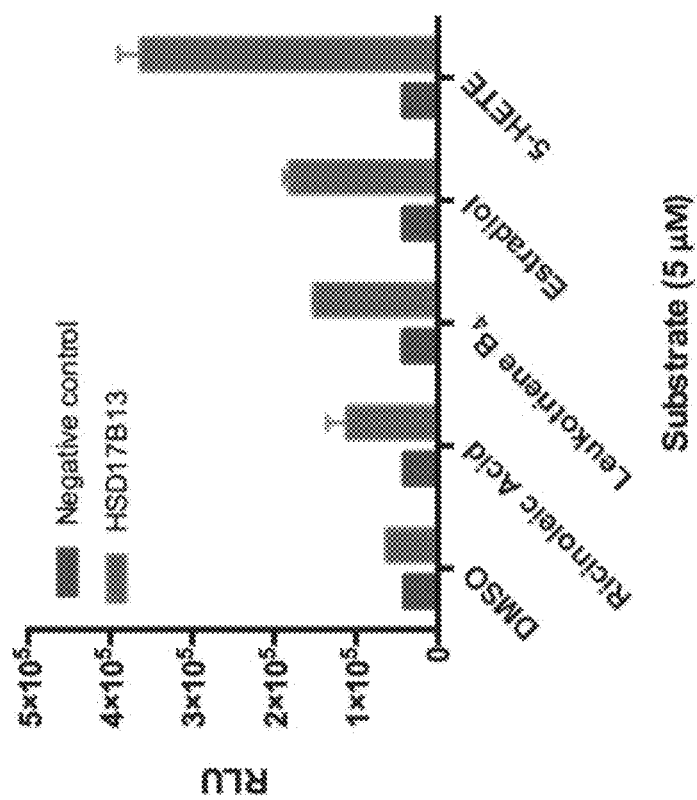
FIG. 3A shows the results of a screen of bioactive lipids with human HSD17B13 using an NADH-linked assay. Leukotriene B4 and ricinoleic acid were identified as representative substrates for HSD17B13. GFP protein was tested in parallel as a negative control. DMSO served as a substrate control. For each set of bars, the left bar is the GFP control and the right bar is the bioactive lipid substrate.
Figure 3B:
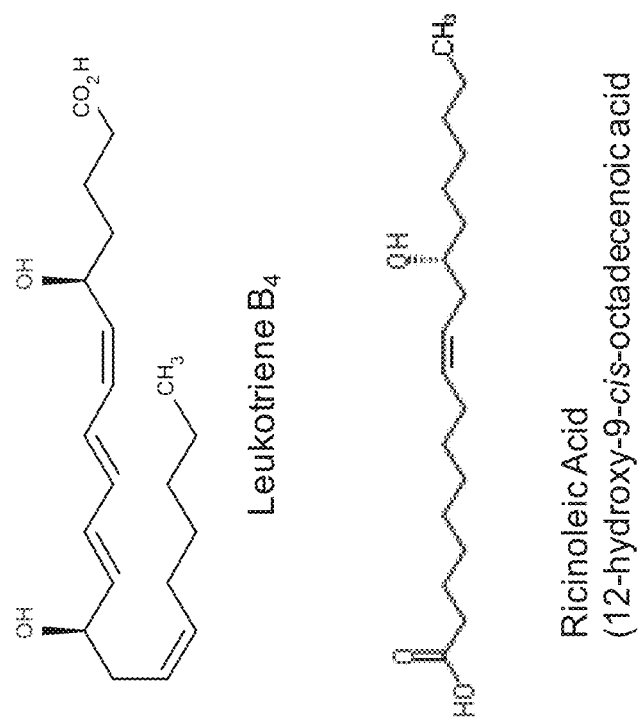
FIG. 3B shows the structure of lipids used in the assay shown in FIG. 3A.

The biochemical assay described in Example 1 was repeated using bioactive lipids as substrates. In brief, 5 μM of each substrate was incubated in 40 μL reactions containing 1 μg of recombinant HSD17B13 (E20-K300) or beta-2 microglobulin (as a negative control) and 100 μM NAD$^+$ in 0.2M Tris-HCl, pH 7.5. After four hours of incubation at room temperature, 10 μL of each reaction was mixed with 10 μL luciferase and read, after 40 minutes, on an Envision Plate Reader (Perkin Elmer). The results are shown in FIG. 3A; chemical formulae for the lipids used in this assay are shown in FIG. 3B. The results show that Leukotriene B4 is a substrate for HSD17B13.

Figure 4:
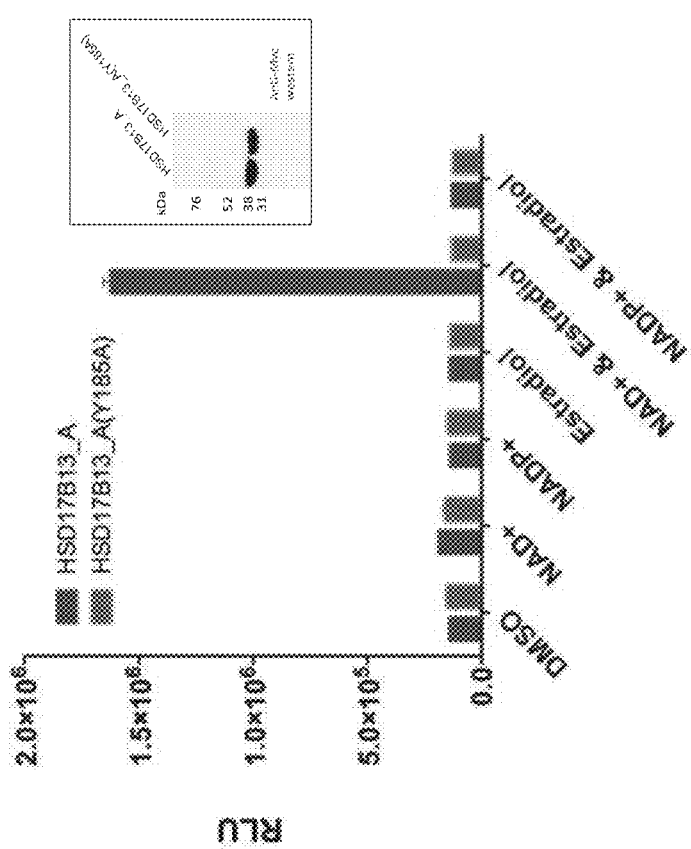
FIG. 4 shows that HSD17B13 uses NAD$^+$ as a cofactor and that mutation of a catalytic site residue (Y185A) of the enzyme abolished the activity. For each set of bars, the left bar is the wild-type HSD17B13 and the right bar is the Y185A mutant form of HSD17B13. The inset is a western blot showing that the wildtype and mutant proteins were expressed at equal levels.

Example 3: Human HSD17B13 Prefers NAD$^+$ as a Cofactor and Mutation of Catalytic Site Residue (Y185A) or Heat Inactivation Eliminates Enzymatic Activity An NADH enzymatic assay was employed using the following reaction conditions: 0.1 M Potassium phosphate buffer pH 7.5, 0.5 mM NAD(P)$^+$, 75 μM Estradiol in DMSO 2% reaction volume 1 μl of purified enzyme at a final reaction volume of 100 μL, with a 24 hr incubation at 25 degrees C. After incubation, 20 μL reaction above+20 μL luciferase were incubated at room temperature for 1 hour and read on an Envision Plate Reader (Perkin Elmer). The results are shown in FIG. 4. These results show that NAD$^+$ is the preferred cofactor of HSD17B13, and that mutation of catalytic site of the protein at residue 185 (Tyr to Ala) eliminated catalytic conversion of estradiol.

Figure 5:
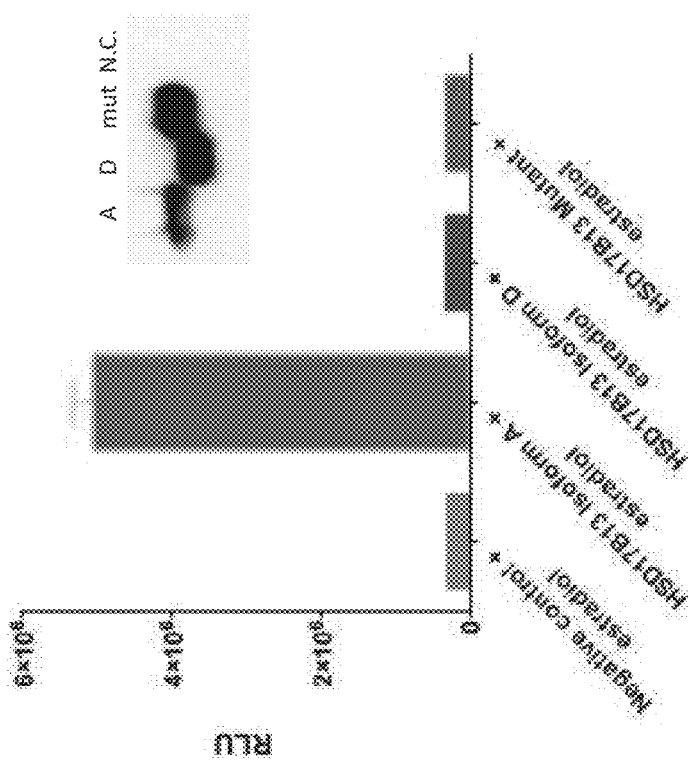
FIG. 5 shows that purified isoform D of HSD17B13 cannot utilize estradiol as a substrate. The inset shows a western blot showing that comparable amounts of wildtype (A isoform), truncation (D isoform), and mutant A isoform (Y185A) of HSD17B13 protein was used in the assay.

Example 4: Human HSD17B13 Isoform A is Active Whereas the Corresponding D Isoform is Inactive Against Steroids The wildtype (A isoform of HSD17B13) was compared against the loss of function truncation isoform D in an NADH enzymatic assay. The reaction conditions were as follows: 0.1 M potassium phosphate buffer at pH 7.5, 0.5 mM NAD(P)$^+$, 75 μM Estradiol in DMSO 2% reaction and purified enzyme in the amount shown in the western blot (FIG. 5 insert), with a final reaction volume of 100 μL. The western showed that equivalent amounts of protein were added; estimated that about 10 ng of each protein used. The reaction proceeded for a 24 hr incubation period at 25 degrees C. After incubation, 20 μL of the reaction mixture and 20 μL luciferase were incubated at room temperature for 1 hour and read on an Envision Plate Reader (Perkin Elmer). The results are shown in FIG. 5. The results show that the purified A isoform of HSD17B13 actively converted estradiol, but neither the truncated D isoform nor the inactivated Y185A mutant of Isoform A could use estradiol as a substrate under these experimental conditions.

These results were confirmed in a cell-based assay. The assay was as described in Example 1, with the A and D isoforms of HSD17B13 used, and with estradiol (E2), androstanediol (M634), estrone (E1), and androsterone (M624) used as substrates. Protein expression was confirmed by Western blot (FIG. 6, insert).

HEK293 cells overexpressing HSD17B13 isoform A, HSD17B13 isoform D, or green fluorescent protein (GFP) were plated into a 24 well plate (1×10$^5$ cells with 500 μL of culture media/well). Each tested compound was added to an individual well at 1 μM. After 2 hrs or 48 hrs incubation, 40 μL of culture medium was transferred from each well into a 96 well plate for LC-MS analysis as described in Example 1.

Figure 6:
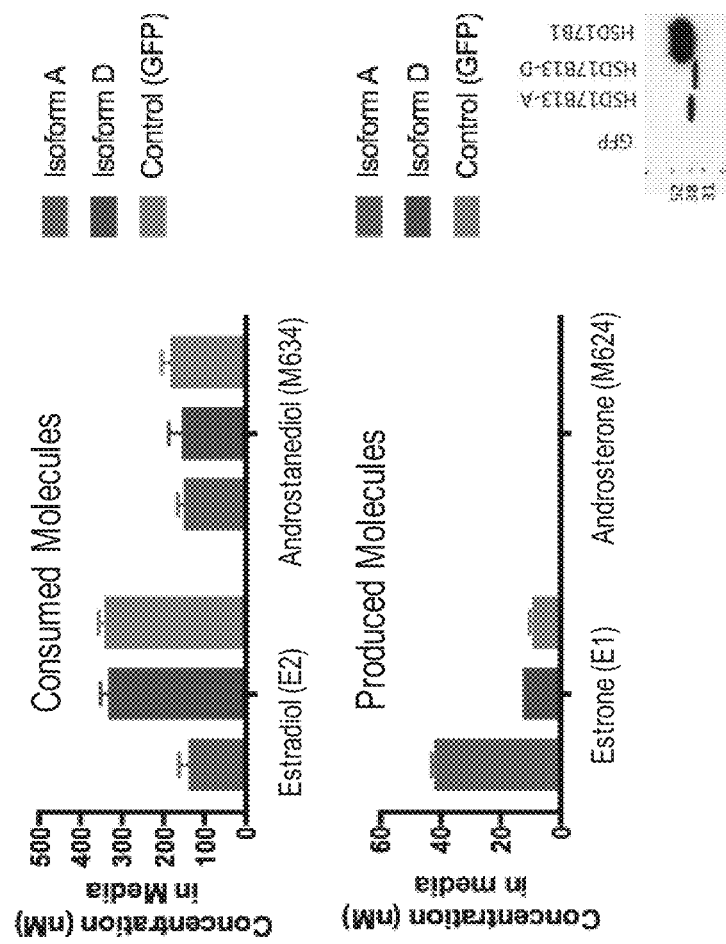
FIG. 6 shows that isoform D of HSD17B13 has no activity against estradiol or androstanediol in a cell-based assay.

The results of the cell-based assay are shown in FIG. 6. The results showed that the A isoform, but not the D isoform, had catalytic activity in the cell-based assay under these experimental conditions.

Example 5: NAD(P)H Assay can be Used for Substrate and Inhibitor Screening as Demonstrated with HSD17B1 Enzyme The HSD17B1 enzyme was first tested to demonstrate compatibility of HSD17B13 with a biochemical inhibitor assay. Dose dependency was assessed. For the dose dependence experiment, the reaction conditions were as follows: 1 μM NADP and 13.3 μM estradiol (E2) were incubated with increasing amounts of recombinant HSD17B1 for 40 minutes at 37 degrees C. in a 20 μL reaction volume. The reaction was stopped with the addition of 2.5 μL 0.4N NaOH, then 2.5 μL of neutralization buffer (equal parts 0.4N HCl and 0.5 M Trizma). The reaction was then mixed with an equal volume of luciferase reagent and read at 40 minutes on an Envision Plate Reader (Perkin Elmer).

For equilin inhibition: 1 μM NADP and 3 μM estradiol (E2) were incubated with 270 nM HSD17B1 (Creative Biomart, cat #HSD17B1-586H) or buffer in the presence of increasing concentrations of equilin (Sigma, cat #E8126) for 40 minutes at 37 degrees C. in a 20 μL reaction volume. The reaction was stopped with the addition of 2.5 μL 0.4N NaOH, then 2.5 μL of neutralization buffer (equal parts 0.4N HCl and 0.5 M Trizma). The reaction was then mixed with an equal volume of luciferase reagent and read at 40 minutes on an Envision Plate Reader (Perkin Elmer).

Figure 7A:
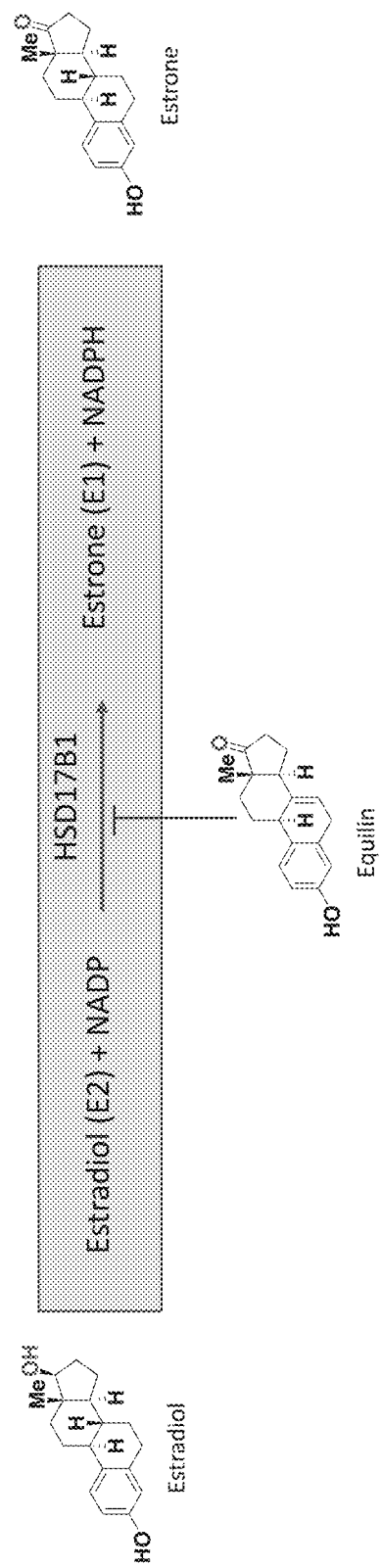
FIG. 7A shows the conversion assay of estradiol to estrone by HSD17B1, and inhibition of HSD17B1 with equilin.
Figure 7B:
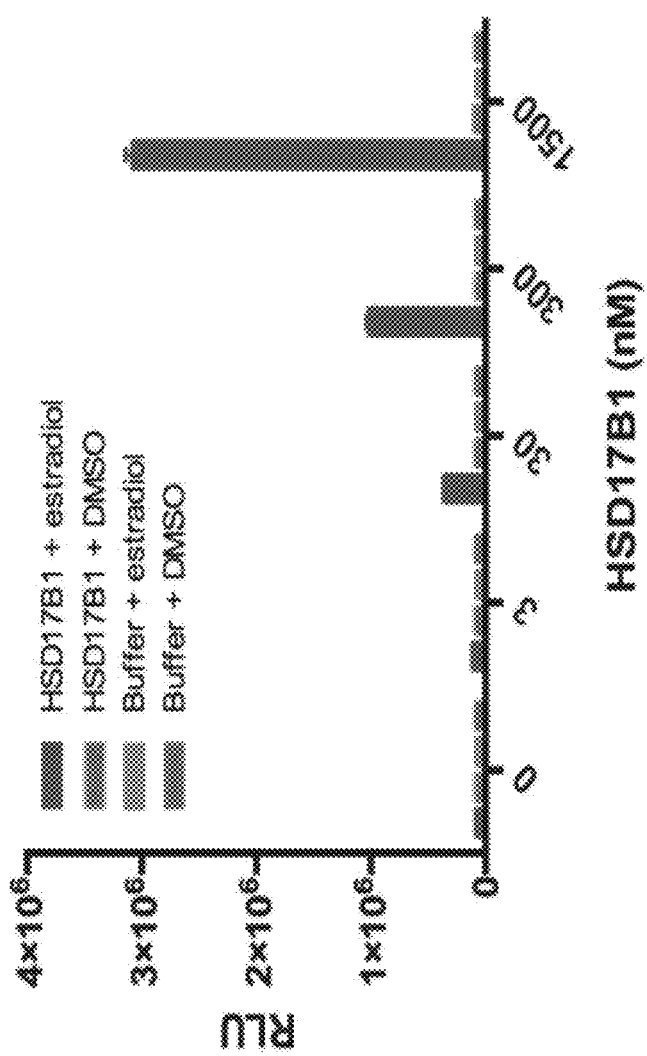
FIG. 7B shows dose-dependence of HSD17B1 activity in a biochemical luciferin assay. The left-most bar in each concentration set is HSD17B1+estradiol, the second from the left is HSD17B1+DMSO, the second from the right is buffer +estradiol, and the right-most bar is buffer+DMSO. The molecule was incubated in the presence of 1 micromolar NADP and 13.3 micromolar estradiol (E2).
Figure 7C:
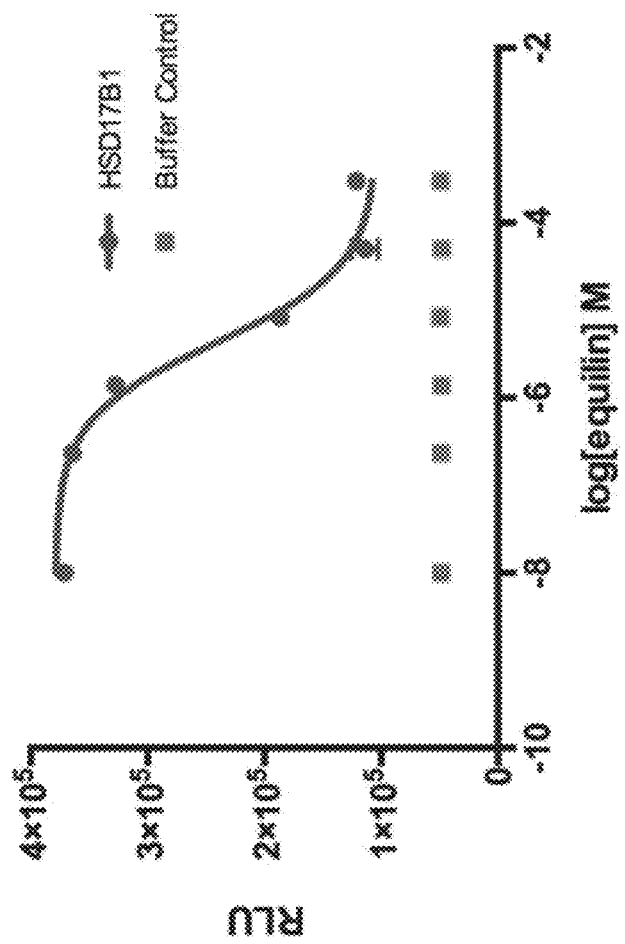
FIG. 7C shows that equilin inhibits HSD17B1 activity at an IC$_{50}$ of 4.3 micromolar. 270 nM of enzyme was incubated with 1 micromolar NADP and 3 micromolar estradiol, with a dose response for equilin.

The results are shown in FIGS. 7B and 7C. FIG. 7A illustrates the conversion reaction of estradiol to estrone, as catalyzed by HSD17B1, which can be inhibited by equilin (Sawicki M W et al. (1999) Proc. Natl. Acad. Sci. USA, 96:840-5). FIG. 7B shows the dose-dependence on enzymatic activity. FIG. 7C shows that equilin inhibits HSD17B1 activity (IC$_{50}$=4.3 μM).

Figure 8A:
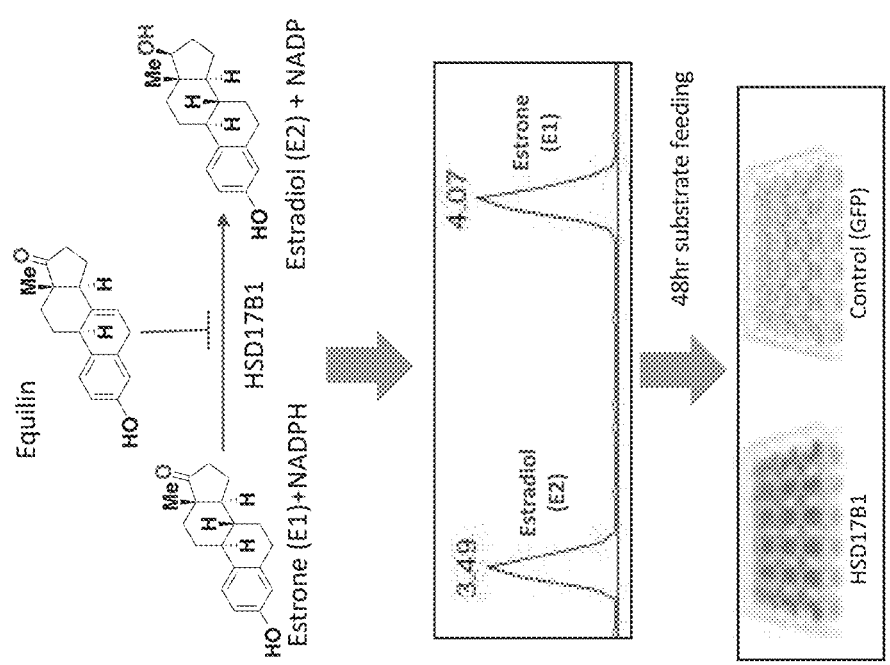
FIG. 8A shows that equilin inhibits conversion of estrone to estradiol by HSD17B1 in a cell-based assay.
Figure 8B:
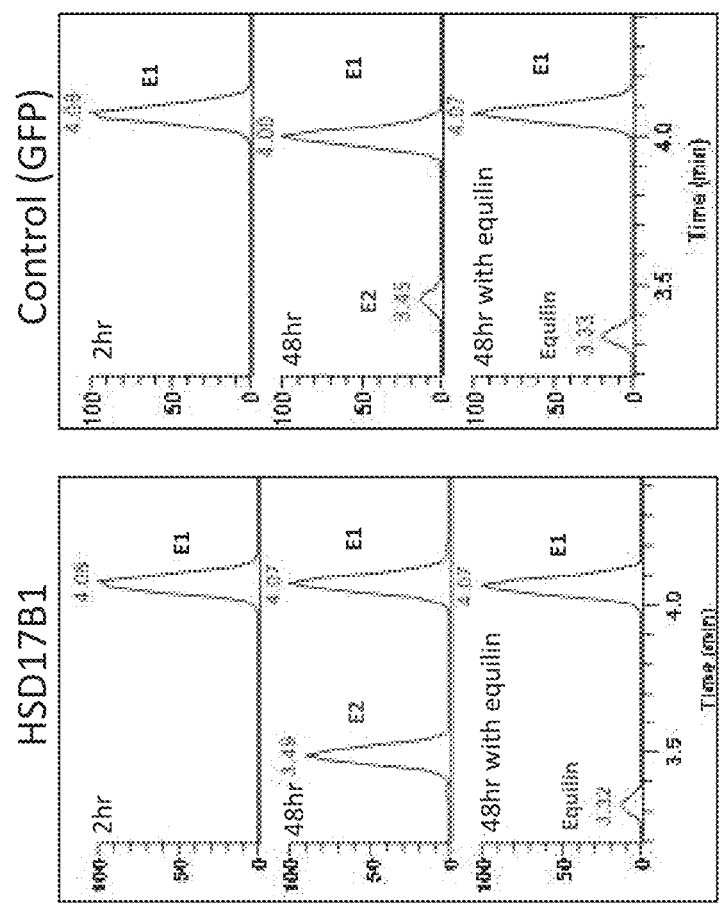
FIG. 8B shows the results of the inhibition as quantified by LC-MS.
Figure 8C:
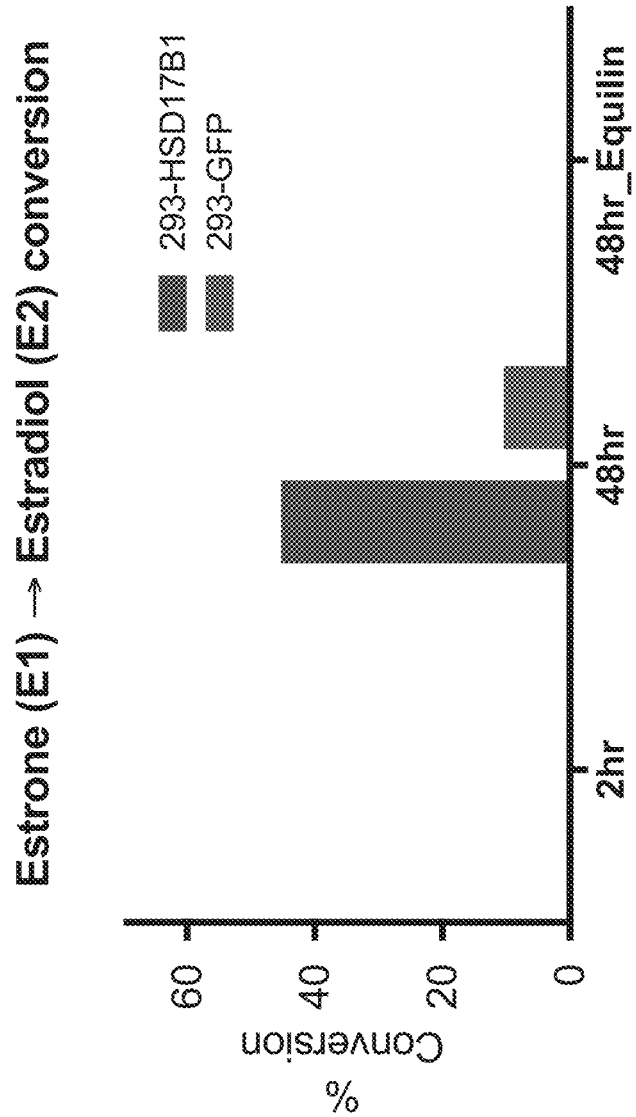
FIG. 8C shows the percentage of estradiol conversion over time, and that equilin inhibits this conversion over the 48 hour period.

The capacity of HSD17B1 to convert estrone to estradiol, and the capacity of equilin to inhibit HSD17B1 was confirmed in a cell-based assay. Liquid chromatography and mass spectrometry (LC-MS) was used to measure estrone and estradiol concentration over time. The results are shown in FIGS. 8A through 8C. The results of the cell based assay show that conversion of hormone substrates in a cell-based assay can be detected by LC-MS. The results further show that the conversion of estrone to estradiol by HSD17B1 can be inhibited by equilin.

Example 6: Substrate Screening of Steroid and Bioactive Lipid Libraries Against Purified Recombinant HSD17B13

Figure 9:
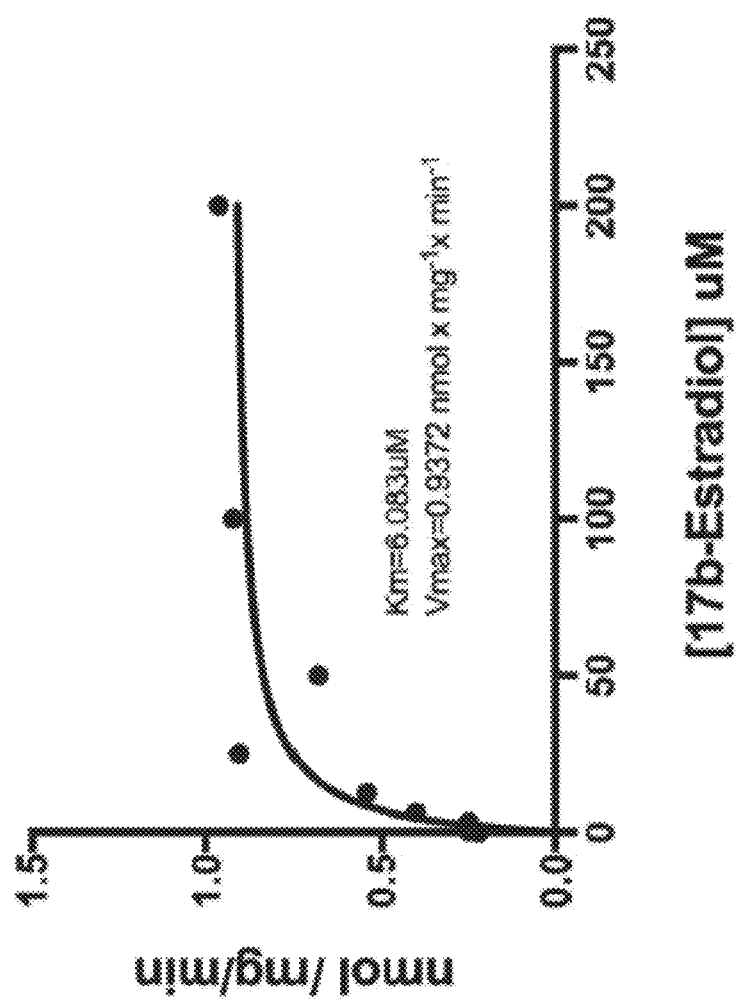
FIG. 9 shows HSD17B13 enzymatic activity on enzymatic conversion of estradiol (Vmax and Km values), which resulted in oxidation of a hydroxyl to a ketone group.
Figure 10B:
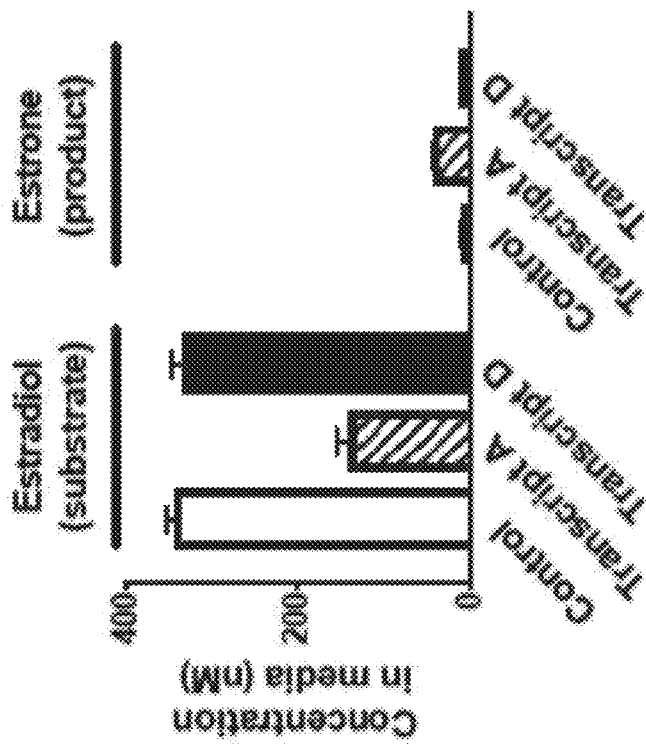
FIGS. 10A and 10B show that HSD17B13 isoform D showed greatly reduced activity towards estradiol in vitro (see, FIG. 10A) and in cell-based enzymatic conversion assays (see, FIG. 10B) when compared to HSD17B13 isoform A.
Figure 10A:
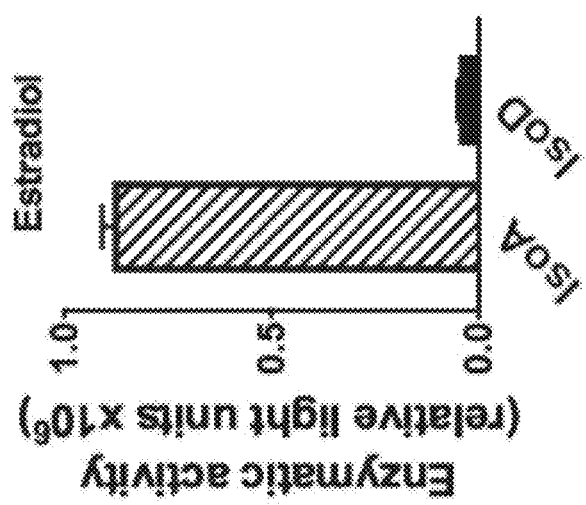

To understand the functional consequences of premature truncation of the HSD17B13 protein due to rs72613567:TA (the associated variant, rs72613567, is an insertion of an adenine adjacent to the donor splice site of exon six (TA allele)), the enzymatic activity of isoforms A and D was evaluated in vitro using recombinant protein and nicotinamide adenosine dinucleotide as cofactor. Reactions were performed in a final volume of 40 μl of assay buffer (0.2 M Tris-HCl, pH 7.5) which contained 500 μM NAD$^+$, 5 μM bioactive lipid or 50 μM steroid (all in a final concentration of 5% DMSO), and 100 ng of recombinant human HSD17B13. Reactions were incubated for 3 hours, at 23° C., after which an equal volume detection reagent was added. Following a 1 hour incubation at 23° C., the relative light units (RLUs) were measured on an Envision Plate Reader (Perkin Elmer). Raw RLU values were normalized as percent of control (50 μM estradiol) following subtraction of negative control (5% DMSO) using the following formula: Percent of control (POC)=100×(Sample (RLU)−Negative $CTRL_{average}$)/(Positive $CTRL_{average}$−Negative $CTRL_{average}$). 265 unique putative substrates (see, Table 1) were tested, and identified steroid substrates and bioactive lipids (e.g., leukotriene B4) as enzymatic substrates of HS17B13. Subsequent characterization of HSD17B13 enzymatic activity was focused on enzymatic conversion of estradiol ($V_{max}$ and $K_m$ values in FIG. 9), which resulted in oxidation of a hydroxyl to a ketone group. HSD17B13 isoform D showed greatly reduced activity towards estradiol in vitro (see, FIG. 10A) and in cell-based enzymatic conversion assays (see, FIG. 10B) when compared to HSD17B13 isoform A.

TABLE 1

Evaluation of Putative HSD17B13 Substrates

| Compound Name | HSD17B13 Enzymatic Activity | |
|---|---|---|
| | Relative Light Units | Percent Estradiol Control |
| Bioactive Lipid Library | | |
| (±)10-HDHA | 801680 | 38.28 |
| (±)11-HDHA | 1259280 | 72.31 |
| (±)11-HEDE | 1334080 | 77.87 |
| (±)11-HEPE | 791920 | 37.56 |
| (±)11-HETE | 767720 | 35.76 |
| (±)11(12)-DiHET | 599000 | 20.69 |
| (±)11(12)-EET | 306600 | 1.47 |
| (±)12-HEPE | 761600 | 35.30 |
| (±)12-HETE | 1324640 | 77.17 |
| (±)12-HpETE | 165800 | −9.27 |
| (±)12(13)-EpOME | 358360 | 2.52 |
| (±)13-HDHA | 1154720 | 64.54 |
| (±)13-HODE | 954080 | 49.62 |
| (±)14(15)-DiHET | 403560 | 5.93 |
| (±)14(15)-DiHETE | 356480 | 2.37 |
| (±)14(15)-EET | 305720 | 1.41 |
| (±)14(15)-EpETE | 306600 | 1.86 |
| (±)15-HEDE | 1430720 | 85.06 |
| (±)15-HEPE | 578600 | 21.70 |
| (±)15-HETE | 47880 | 30.81 |
| (±)16(17)-EpDPA | 274120 | −0.71 |
| (±)17-HDHA | 492440 | 15.29 |
| (±)17(18)-DiHETE | 369120 | 3.33 |
| (±)17(18)-EpETE | 316240 | 2.19 |
| (±)19(20)-DiHDPA | 827600 | 37.95 |
| (±)19(20)-EpDPA | 300600 | 1.38 |
| (±)20-HDHA | 1400640 | 82.82 |
| (±)4(5)-EpDPA methyl ester | 338320 | 1.00 |
| (±)5-HEPE | 344480 | 4.85 |
| (±)5-HETE | 431960 | 10.79 |
| (±)5-HETE lactone | 348120 | 4.56 |
| (±)5-HETE methyl ester | 337600 | 3.78 |
| (±)5(6)-DiHET | 353120 | 4.93 |
| (±)5(6)-DiHET lactone | 411120 | 6.50 |
| (±)5(6)-EET | 360960 | 5.51 |
| (±)5(6)-EET Ethanolamide | 450160 | 9.45 |
| (±)7-HDHA | 361320 | 5.54 |
| (±)8-HDHA | 773120 | 36.16 |
| (±)8-HEPE | 472800 | 13.83 |
| (±)8-HETE | 592720 | 22.75 |
| (±)8(9)-DiHET | 472120 | 11.11 |
| (±)9-HEPE | 699960 | 30.72 |
| (±)9-HETE | 1110120 | 61.22 |
| (±)9-HODE | 695320 | 30.38 |
| (±)9(10)-DiHOME | 391000 | 4.98 |
| (±)9(10)-EpOME | 354560 | 2.23 |
| 10-Nitrooleate | 28200 | −22.42 |
| 11-dehydro Thromboxane B2 | 349160 | 5.22 |
| 11-dehydro Thromboxane B2-d4 | 366280 | 3.11 |
| 11-dehydro Thromboxane B3 | 322480 | 3.11 |
| 11-dehydro-2,3-dinor Thromboxane B2 | 183120 | −7.90 |
| 11(12)-EET Ethanolamide | 440800 | 8.74 |
| 11(R)-HEDE | 1674200 | 103.16 |
| 11(R)-HEPE | 940920 | 48.64 |
| 11(R)-HETE | 1064120 | 57.80 |
| 11(S)-HEDE | 1056440 | 57.23 |
| 11(S)-HEPE | 1525600 | 92.11 |
| 11(S)-HETE | 696400 | 30.46 |
| 11β-13,14-dihydro-15-keto Prostaglandin F2α | 310000 | 2.13 |
| 11β-Misoprostol | 331200 | 3.80 |
| 11β-Prostaglandin E2 | 354840 | 5.67 |
| 12-epi Leukotriene B3 | 481880 | 15.71 |
| 12-epi Leukotriene B4 | 389240 | 8.39 |
| 12(R)-HETE | 1932320 | 122.36 |
| 12(S)-HpETE | 199760 | −6.47 |
| 13-epi-12-oxo Phytodienoic Acid | 320640 | 2.97 |
| 13,14-dehydro-15-cyclohexyl Carbaprostacyclin | 356360 | 5.79 |
| 13,14-dihydro-19(R)-hydroxy Prostaglandin E1 | 337040 | 4.26 |
| 13(R)-HODE | 1105960 | 60.91 |
| 13(S)-HODE | 792800 | 37.62 |
| 13(S)-HOTrE | 528240 | 17.95 |
| 13(S)-HOTrE(γ) | 458840 | 12.79 |
| 13(S)-HpODE | 183040 | −7.72 |
| 13(S)-HpOTrE | 35320 | −18.70 |
| 13(S)-HpOTrE(γ) | 268840 | −1.34 |
| 14(15)-EET Ethanolamide | 428760 | 7.83 |
| 15-deoxy-Δ12,14-Prostaglandin J2-biotin | 252400 | −2.43 |
| 15-OxoEDE | 261480 | −1.88 |
| 15-OxoETE | 616120 | −8.98 |
| 15(R)-HEDE | 1862960 | 117.20 |
| 15(R)-HETE | 701120 | 61.00 |
| 15(R),19(R)-hydroxy Prostaglandin E1 | 333200 | 3.96 |
| 15(R),19(R)-hydroxy Prostaglandin E2 | 346000 | 4.97 |
| 15(R),19(R)-hydroxy Prostaglandin F2α | 382720 | 7.88 |
| 15(S)-Fluprostenol isopropyl ester | 410960 | 10.11 |
| 15(S)-HEDE | 1060680 | 57.54 |
| 15(S)-HEPE | 505240 | 16.24 |
| 15(S)-HETE | 1107240 | 24.49 |
| 15(S)-HETE Ethanolamide | 535680 | 19.97 |
| 15(S)-HETrE | 638320 | 26.14 |
| 15(S)-HpEDE | 232720 | −4.02 |
| 15(S)-HpEPE | 316200 | 2.18 |
| 16,16-dimethyl Prostaglandin E2 p-(p-acetamidobenzamido) phenyl ester | 322280 | 3.10 |
| 17-trans Prostaglandin F3α | 371720 | 7.01 |
| 19(R)-hydroxy Prostaglandin A2 | 323320 | 3.18 |
| 19(R)-hydroxy Prostaglandin E1 | 333160 | 3.96 |
| 19(R)-hydroxy Prostaglandin E2 | 347280 | 5.07 |
| 19(R)-hydroxy Prostaglandin F1α | 207560 | −5.97 |
| 19(R)-hydroxy Prostaglandin F2α | 371400 | 6.98 |
| 2,3-dinor Prostaglandin E1 | 344240 | 4.83 |
| 2,3-dinor Thromboxane B1 | 364840 | 3.01 |
| 2,3-dinor-11β-Prostaglandin F2α | 265000 | −1.43 |
| 2,3-dinor-6-keto Prostaglandin F1α (sodium salt) | 341800 | 4.64 |
| 2,3-dinor-8-iso Prostaglandin F2α | 230040 | −4.19 |
| 20-carboxy Arachidonic Acid | 293760 | −2.36 |
| 20-carboxy Leukotriene B4 | 400440 | 9.28 |
| 20-HETE | 332640 | 0.57 |
| 20-HETE Ethanolamide | 879760 | 41.89 |
| 20-hydroxy Leukotriene B4 | 654120 | 29.33 |
| 20-hydroxy Prostaglandin E2 | 348240 | 5.15 |
| 20-hydroxy Prostaglandin F2α | 378680 | 7.56 |
| 5-iPF2α-VI | 293200 | 0.80 |
| 5-OxoETE | 261280 | −1.90 |
| 5-trans Fluprostenol isopropyl ester | 551400 | 21.21 |

TABLE 1-continued

Evaluation of Putative HSD17B13 Substrates

| Compound Name | HSD17B13 Enzymatic Activity | |
|---|---|---|
| | Relative Light Units | Percent Estradiol Control |
| 5,6-dehydro Arachidonic Acid | 210160 | −8.68 |
| 5(6)-EpETE methyl ester | 337400 | 0.93 |
| 5(S)-HEPE | 429120 | 10.58 |
| 5(S)-HETE | 430800 | 10.71 |
| 5(S)-HETE lactone | 288400 | 0.12 |
| 5(S)-HpETE | 225600 | −4.55 |
| 5(S),15(S)-DiHETE | 486600 | 14.86 |
| 5(S),6(R)-DiHETE | 166040 | 1.66 |
| 5(S),6(S)-DiHETE | 309080 | 4.07 |
| 6-trans Leukotriene B4 | 1209480 | 68.61 |
| 6,15-diketo-13,14-dihydro Prostaglandin F1α | 262680 | −1.61 |
| 6(S)-Lipoxin A4 | 383000 | 7.90 |
| 8-iso Prostaglandin F3α | 361040 | 6.16 |
| 8-iso-13,14-dihydro-15-keto Prostaglandin F2α | 212520 | −5.58 |
| 8-iso-15-keto Prostaglandin E2 | 262160 | −1.65 |
| 8-iso Prostaglandin F2α | 312360 | 2.31 |
| 8(9)-EET Ethanolamide | 446000 | 9.14 |
| 8(S)-HETrE | 412960 | 9.38 |
| 8(S),15(S)-DiHETE | 410440 | 9.19 |
| 9-Nitrooleate | 31600 | −22.16 |
| 9-OxoODE | 359280 | 5.39 |
| 9(R)-HETE | 1656640 | 101.86 |
| 9(R)-HODE | 413280 | 9.40 |
| 9(S)-HEPE | 564200 | 20.63 |
| 9(S)-HETE | 497640 | 15.68 |
| 9(S)-HODE | 539560 | 18.79 |
| 9(S)-HOTrE | 586800 | 22.31 |
| 9(S)-HpODE | 219240 | −5.03 |
| Calcitriol | 336600 | 0.88 |
| Carbaprostacyclin | 380280 | 7.68 |
| Carbocyclic Thromboxane A2 | 309000 | 2.05 |
| Cholesteryl Linoleate Hydroperoxides | 256120 | −2.28 |
| Ciprostene (calcium salt) | 360560 | 6.12 |
| D-myo-Inositol-1,2,3,4-tetraphosphate (sodium salt) | 447960 | 9.28 |
| D-myo-Inositol-1,2,3,5-tetraphosphate (sodium salt) | 430640 | 7.98 |
| D-myo-Inositol-1,2,3,6-tetraphosphate (sodium salt) | 424280 | 7.49 |
| D-myo-Inositol-1,2,4,5-tetraphosphate (sodium salt) | 403880 | 5.95 |
| D-myo-Inositol-1,2,4,5,6-pentaphosphate (sodium salt) | 398080 | 5.52 |
| D-myo-Inositol-1,3-diphosphate (sodium salt) | 487280 | 12.25 |
| D-myo-Inositol-1,3,4,5-tetraphosphate (sodium salt) | 358920 | 2.56 |
| D-myo-Inositol-1,4-diphosphate (sodium salt) | 439280 | 8.63 |
| D-myo-Inositol-1,4,5-triphosphate (potassium salt) | 358400 | 2.52 |
| D-myo-Inositol-1,5-diphosphate (sodium salt) | 443840 | 8.97 |
| D-myo-Inositol-2,3,4,5-tetraphosphate (ammonium salt) | 372320 | 3.57 |
| D-myo-Inositol-2,4-diphosphate (sodium salt) | 306720 | −1.38 |
| D-myo-Inositol-3,4,5-triphosphate (sodium salt) | 400520 | 5.70 |
| D-myo-Inositol-4-phosphate (ammonium salt) | 408880 | 6.33 |
| D-myo-Inositol-4,5-diphosphate (sodium salt) | 281680 | −3.27 |
| Fluprostenol isopropyl ester | 467040 | 14.54 |
| HPF | 273840 | −0.73 |
| Hyperforin | 23920 | −22.74 |
| I-BOP | 358960 | 6.00 |
| I-SAP | 245520 | −2.97 |
| Iloprost | 358880 | 5.99 |
| Lactacystin | 328520 | 0.26 |
| Leukotriene A3 methyl ester | 990560 | 55.92 |
| Leukotriene A4 methyl ester | 463120 | 14.23 |
| Leukotriene B3 | 2077280 | 141.62 |
| Leukotriene B4 | 1743000 | 115.40 |
| Leukotriene B4 dimethyl amide | 1910040 | 128.60 |
| Leukotriene B4 Ethanolamide | 1948920 | 131.68 |
| Leukotriene F4 | 400400 | 9.27 |
| Lipoxin A4 | 352680 | 2.09 |
| MK-571 | 281520 | −0.12 |
| PGPC | 371440 | 6.98 |
| Prostaglandin A1-biotin | 309320 | 2.07 |
| Prostaglandin A3 | 227000 | −4.43 |
| Prostaglandin D2-biotin | 367880 | 3.24 |
| Prostaglandin D3 | 298960 | 1.25 |
| Prostaglandin E2 p-benzamidophenyl ester | 404280 | 9.58 |
| Prostaglandin E2-biotin | 389960 | 4.90 |
| Prostaglandin E3 | 379960 | 7.66 |
| Prostaglandin F2α-biotin | 340200 | 1.14 |
| Prostaglandin F3α | 385360 | 8.08 |
| Prostaglandin H1 | 145840 | −10.85 |
| Prostaglandin H2 | 166640 | −9.20 |
| Prostaglandin I3 (sodium salt) | 333560 | 3.99 |
| Prostaglandin K1 | 223160 | −4.74 |
| Prostaglandin K2 | 155600 | −10.08 |
| PtdIns-(3,4,5)-P3 (1,2-dipalmitoyl) (sodium salt) | 334600 | 0.72 |
| PtdIns-(3,4)-P2 (1,2-dipalmitoyl) (sodium salt) | 351680 | 2.01 |
| PtdIns-(3)-P1 (1,2-dioctanoyl) (sodium salt) | 319680 | −0.40 |
| PtdIns-(3)-P1 (1,2-dipalmitoyl) (ammonium salt) | 15520 | −23.38 |
| PtdIns-(4,5)-P2 (1,2-dioctanoyl) (sodium salt) | 348680 | 1.79 |
| PtdIns-(4,5)-P2 (1,2-dipalmitoyl) (ammonium salt) | 24120 | −22.73 |
| PtdIns-(4)-P1 (1,2-dipalmitoyl) (ammonium salt) | 123240 | −15.24 |
| PtdIns-(5)-P1 (1,2-dipalmitoyl) (ammonium salt) | 19160 | −23.10 |
| tetranor-12(R)-HETE | 708640 | 31.37 |
| tetranor-12(S)-HETE | 379280 | 4.10 |
| tetranor-PGDM-d6 | 375520 | 3.81 |
| tetranor-PGEM | 348440 | 5.17 |
| tetranor-PGFM | 367640 | 6.68 |
| Thromboxane B3 | 348080 | 5.14 |
| U-51605 | 278680 | −0.35 |
| U-75302 | 425520 | 7.59 |
| Δ12-Prostaglandin J2 | 343320 | 4.76 |
| Δ17-6-keto Prostaglandin F1α | 286120 | 0.24 |
| Estradiol Control | 1548190 | 100.00 |
| DMSO | 283090 | 0.00 |
| Steroid Library | | |
| Apigenin | 24440 | −2.38 |
| (2a,3a,52,17b)-Androstan-17ol,2,3-epithio-17-methyl | 100160 | −1.06 |
| (2b,3a,5a,16b,17b)-2-(4-morpholinyl)-16-(1-pyrrolidinyl)androsta | 191960 | 0.55 |
| 11-oxo-androsterone | 196640 | 0.63 |
| 11-oxo-etiocholanolone | 195960 | 0.62 |
| 11beta-Hydroxyandrosterone | 224720 | 1.12 |
| 16alpha-Hydroxyandrosterone | 221840 | 1.07 |
| 18beta-Glycyrrhetinic acid | 32720 | −2.23 |
| 2alpha,3alpha,5alpha,16beta-16-(1-pyrrolidinyl)-2,3-Epoxyandr | 166400 | 0.10 |
| 2alpha,3alpha,5alpha,16beta,17beta-16-(1-pyrrolidinyl)-2,3-e | 103360 | −1.00 |
| 3b,5-Dihydroxy-6b,7b:15b,16b-dimethylene-5b-androstan17-one | 183120 | 0.39 |
| 5a-androstanedione | 181840 | 0.37 |
| 5alpha-Androsta-2,16-dien-17-yl acetate | 197640 | 0.65 |
| 5alpha-Androstane-3,11,17-trione | 228280 | 1.18 |
| 5alpha-androstane-3beta,17beta-diol | 398600 | 4.16 |
| 5alpha-dihydrocortisol | 139720 | −0.36 |
| 5alpha-Tetrahydrocortisol | 229040 | 1.20 |
| 6-ethylchenodeoxycholic acid | 76200 | −1.47 |
| Aldosterone | 217400 | 0.99 |
| Androstanediol | 488440 | 5.73 |
| Androstanolone 17-benzoate | 217200 | 0.99 |
| Androstanolone acetate | 200560 | 0.70 |
| Androstenediol | 1364160 | 21.02 |
| Androstenedione | 172400 | 0.21 |
| Androsterone | 158120 | −0.04 |
| Beta-estradiol | 4292760 | 72.17 |
| Beta-sitosterol | 168880 | 0.14 |

TABLE 1-continued

Evaluation of Putative HSD17B13 Substrates

| Compound Name | HSD17B13 Enzymatic Activity | |
|---|---|---|
| | Relative Light Units | Percent Estradiol Control |
| Corticosterone | 215320 | 0.96 |
| Corticosterone 21-acetate | 190160 | 0.52 |
| Cortisol | 40080 | −2.10 |
| Cortisone | 204080 | 0.76 |
| Cortisone 21-acetate | 200240 | 0.69 |
| Dehydroepiandrosterone | 196240 | 0.62 |
| DHT | 1886360 | 30.14 |
| Dromostanolone proprionate | 212040 | 0.90 |
| Epiandrosterone | 185800 | 0.44 |
| Epiandrosterone acetate | 210960 | 0.88 |
| Equilin | 186840 | 0.46 |
| Estradiol | 5070800 | 85.76 |
| Estrone | 186200 | 0.45 |
| Formestane | 196520 | 0.63 |
| Glycyrrhizic acid | 163600 | 0.05 |
| Honokiol | 52920 | −1.88 |
| Oleic Acid | 17520 | −2.50 |
| Oxymetholone | 92000 | −1.20 |
| Prednisone | 196720 | 0.63 |
| Pregnanetriol | 163920 | 0.06 |
| Progesterone | 175680 | 0.26 |
| Rostafuroxin | 187520 | 0.47 |
| Spironolactone | 184280 | 0.41 |
| Stanazol | 140840 | −0.35 |
| Superdrol | 105920 | −0.95 |
| Testosterone | 1125600 | 16.86 |
| TetrahydroCortisone | 232320 | 1.25 |
| Trilostane | 1896560 | 30.32 |
| Estradiol Control | 5885860 | 100.00 |
| DMSO | 160593 | 0.00 |

Example 7: Substrate Screening of Steroids Against Various HSD17B Family Member Proteins In order to determine specificity of compounds with inhibitory activity against HSD17B13, assays for selected members of the HSD17B family which includes HSD17B1-HSD17B14 were established. As a first step, selected family members were expressed, purified and tested for activity a using a steroid substrate panel. Substrates from the steroid panel were tested at 50 μM, using the standard assay protocol. Activity against the substrates for each HSD17B family member were normalized to Percent of Control (POC). The control, estradiol, was set as 100%. Substrates that showed>30% of control for any HSD17B member are captured in Table 2.

TABLE 2

Steroid substrates with POC >30 against selected HSD17B family members

| | HSD17B FAMILY MEMBER | | | | | |
|---|---|---|---|---|---|---|
| | B1 | B2 | B4 | B5 | B10 | B11 |
| Estradiol | 100 | 100 | 100 | 100 | 100 | 100 |
| Androstenediol | 0.7 | 57.4 | 76.8 | 0 | 6.4 | 0.0 |
| DHT | 0.4 | 61.2 | 37.1 | 0 | 3.3 | 12.7 |
| Testosterone | 1.1 | 96.2 | 84.6 | 0 | 4.0 | 10.4 |
| Androstanediol | 0.3 | 46.9 | 63.0 | 216 | 1.9 | 0.0 |
| 5alpha-androstane-3beta,17beta-diol | 0.3 | 42.5 | 38.9 | 0 | 1.2 | 0.0 |
| 3a-androstanediol | 0.0 | 6.2 | 16.4 | 196 | −0.4 | 0.0 |
| Corticosterone 21-acetate | −0.1 | 0.0 | 0.1 | 0 | 0.3 | 32.2 |
| Glycyrrhizic acid | −0.1 | 0.0 | 0.7 | 0 | 0.1 | 32.7 |
| Pregnanetriol | −0.1 | 6.1 | 0.4 | 48 | 26.4 | 26.1 |
| 16alpha-hydroxyandrosterone | 0.0 | 1.5 | 0.5 | 45 | 69.7 | 0.0 |
| 11-oxo-etiocholanolone | −0.1 | 0.0 | 0.2 | 13 | 30.7 | 0.0 |
| 5alpha-tetrahydrocortisol | −0.1 | 3.1 | 0.2 | 0 | 46.3 | 0.0 |
| TetrahydroCortisone | 0.0 | 1.0 | 0.5 | 104 | 52.2 | 0.0 |
| 11-oxo-androsterone | 0.0 | 0.0 | 0.4 | 0 | 31.4 | 0.0 |
| Androsterone | 0.0 | 1.0 | 0.3 | 0 | 91.0 | 0.0 |
| 6-ethylchenodeoxycholic acid | 0.0 | 0.1 | 4.6 | 192 | 39.3 | 0.0 |

The following representative embodiments are presented. The embodiments listed below are not meant to be limiting in any manner. For example, although the embodiments listed below specifically recite HSD17B13, the embodiments can be practiced using any of the HSD17B family member proteins described herein.

Embodiment 1

A method for screening a test compound for capability to inhibit hydroxysteroid (17-beta) dehydrogenase 13 (HSD17B13), comprising (a) contacting a first HSD17B13 protein with a test compound, a substrate for HSD17B13, $NAD^+$, a pre-reduced form of luciferin, an enzyme that reduces the pre-reduced form of luciferin to produce luciferin, and luciferase (b) contacting a second HSD17B13 protein with a control, a substrate for HSD17B13, $NAD^+$, a pre-reduced form of luciferin, an enzyme that reduces the pre-reduced form of luciferin to produce luciferin, and luciferase, (c) detecting the emission wavelength of luciferin produced by the luciferase according to step (a) and according to step (b), and identifying the test compound as an inhibitor of HSD17B13 when the emission wavelength of luciferin produced according to step (a) is lower than the wavelength of luciferin produced according to step (b).

Embodiment 2

The method according to embodiment 1, wherein the test compound comprises an organic compound.

Embodiment 3

The method according to embodiment 1, wherein the test compound comprises an inorganic compound.

Embodiment 4

The method according to embodiment 1, wherein the test compound comprises a biomolecule.

Embodiment 5

The method according to any one of embodiments 1 to 4, wherein the test compound is comprised in a composition comprising a carrier.

Embodiment 6

The method according to any one of embodiments 1 to 5, wherein the test compound is comprised in a composition comprising an excipient.

Embodiment 7

The method according to any one of embodiments 1 to 6, wherein the substrate for HSD17B13 comprises a steroid hormone or derivative thereof.

Embodiment 8

The method according to any one of embodiments 1 to 7, wherein the substrate for HSD17B13 comprises an estrogen hormone.

Embodiment 9

The method according to embodiment 8, wherein the estrogen hormone comprises estradiol (E2).

Embodiment 10

The method according to embodiment 8, wherein the estrogen hormone comprises estrone (E1).

Embodiment 11

The method according to any one of embodiments 1 to 7, wherein the substrate for HSD17B13 comprises an androgen hormone.

Embodiment 12

The method according to embodiment 11, wherein the androgen hormone comprises androstaendiol, testosterone, or dihydroxy testosterone (DHT).

Embodiment 13

The method according to any one of embodiments 1 to 7, wherein the substrate for HSD17B13 comprises an androgen hormone derivative.

Embodiment 14

The method according to embodiment 13, wherein the androgen hormone derivative comprises trilostane.

Embodiment 15

The method according to any one of embodiments 1 to 6, wherein the substrate for HSD17B13 comprises a fatty acid.

Embodiment 16

The method according to embodiment 15, wherein the fatty acid comprises ricinoleic acid.

Embodiment 17

The method according to any one of embodiments 1 to 6, wherein the substrate for HSD17B13 comprises a bioactive lipid.

Embodiment 18

The method according to embodiment 17, wherein the bioactive lipid comprises an eicosanoid.

Embodiment 19

The method according to embodiment 17, wherein the eicosanoid comprises a leukotriene.

Embodiment 20

The method according to embodiment 19, wherein the leukotriene comprises leukotriene B4.

Embodiment 21

The method according to any one of embodiments 1 to 20, wherein the first and second HSD17B13 protein comprises human HSD17B13 protein.

Embodiment 22

The method according to any one of embodiments 1 to 21, wherein the first and second HSD17B13 protein comprises an amino acid sequence that is at least about 90% identical to SEQ ID NO:1.

Embodiment 23

The method according to any one of embodiments 1 to 22, wherein the first and second HSD17B13 protein comprises the amino acid sequence of SEQ ID NO:1.

Embodiment 24

A kit, comprising a hydroxysteroid (17-beta) dehydrogenase 13 (HSD17B13) protein or a cell expressing HSD17B13, a substrate for HSD17B13, and instructions for using the HSD17B13 and substrate in a method for screening a test compound for capability to inhibit HSD17B13.

Embodiment 25

The kit according to embodiment 24, wherein the kit comprises a cell expressing HSD17B13, a substrate for HSD17B13, and instructions for using the HSD17B13 and substrate in a method for screening a test compound for capability to inhibit HSD17B13.

Embodiment 26

The kit according to embodiment 24, wherein the kit comprises the HSD17B13 protein, a substrate for HSD17B13, and instructions for using the HSD17B13 and substrate in a method for screening a test compound for capability to inhibit HSD17B13

Embodiment 27

The kit according to embodiment 26, wherein the kit further comprises $NAD^+$, a pre-reduced form of luciferin, an enzyme that reduces the pre-reduced form of luciferin to produce luciferin, and luciferase.

Embodiment 28

The kit according to any one of embodiments 24 to 27, wherein the substrate for HSD17B13 comprises a steroid hormone or derivative thereof.

Embodiment 29

The kit according to any one of embodiments 24 to 28, wherein the substrate for HSD17B13 comprises an estrogen hormone.

Embodiment 30

The kit according to embodiment 29, wherein the estrogen hormone comprises estradiol (E2).

Embodiment 31

The kit according to embodiment 29, wherein the estrogen hormone comprises estrone (E1).

Embodiment 32

The kit according to any one of embodiments 24 to 28, wherein the substrate for HSD17B13 comprises an androgen hormone.

Embodiment 33

The kit according to embodiment 32, wherein the androgen hormone comprises androstaendiol, testosterone, or dihydroxy testosterone (DHT).

Embodiment 34

The kit according to any one of embodiments 24 to 28, wherein the substrate for HSD17B13 comprises an androgen hormone derivative.

Embodiment 35

The kit according to embodiment 34, wherein the androgen hormone derivative comprises trilostane.

Embodiment 36

The kit according to any one of embodiments 24 to 28, wherein the substrate for HSD17B13 comprises a fatty acid.

Embodiment 37

The kit according to embodiment 36, wherein the fatty acid comprises ricinoleic acid.

Embodiment 38

The kit according to any one of embodiments 24 to 28, wherein the substrate for HSD17B13 comprises a bioactive lipid.

Embodiment 39

The kit according to embodiment 38, wherein the bioactive lipid comprises an eicosanoid.

Embodiment 40

The kit according to embodiment 38, wherein the eicosanoid comprises a leukotriene.

Embodiment 41

The kit according to embodiment 39, wherein the leukotriene comprises leukotriene B4.

Embodiment 42

The kit according to any one of embodiments 24 to 41, wherein the HSD17B13 protein comprises human HSD17B13 protein.

Embodiment 43

The kit according to any one of embodiments 24 to 42, wherein the HSD17B13 protein comprises an amino acid sequence that is at least about 90% identical to SEQ ID NO:1.

Embodiment 44

The kit according to any one of embodiments 24 to 43, wherein the HSD17B13 protein comprises the amino acid sequence of SEQ ID NO:1.

Embodiment 45

A method for screening a test compound for capability to inhibit hydroxysteroid (17-beta) dehydrogenase 13 (HSD17B13), comprising (a) contacting a first cell expressing HSD17B13 with a test compound and a substrate for HSD17B13, (b) contacting a second cell expressing HSD17B13 with a control and a substrate for HSD17B13, (c) determining the level of substrate depletion by the cell according to step (a) and according to step (b), and identifying the test compound as an inhibitor of HSD17B13 when the level of substrate depletion according to step (a) is lower than the level of substrate depletion produced according to step (b).

Embodiment 46

The method according to embodiment 45, wherein the first cell and the second cell are mammalian cells.

Embodiment 47

The method according to embodiment 46, wherein the mammalian cells are HEK 293 cells.

Embodiment 48

The method according to any one of embodiments 45 to 47, wherein the test compound comprises an organic compound.

Embodiment 49

The method according to any one of embodiments 45 to 47, wherein the test compound comprises an inorganic compound.

Embodiment 50

The method according to any one of embodiments 45 to 47, wherein the test compound comprises a biomolecule.

Embodiment 51

The method according to any one of embodiments 45 to 50, wherein the test compound is comprised in a composition comprising a carrier.

Embodiment 52

The method according to any one of embodiments 45 to 51, wherein the test compound is comprised in a composition comprising an excipient.

Embodiment 53

The method according to any one of embodiments 45 to 52, wherein the substrate for HSD17B13 comprises a steroid hormone or derivative thereof.

Embodiment 54

The method according to any one of embodiments 45 to 53, wherein the substrate for HSD17B13 comprises an estrogen hormone.

Embodiment 55

The method according to embodiment 54, wherein the estrogen hormone comprises estradiol (E2).

Embodiment 56

The method according to embodiment 54, wherein the estrogen hormone comprises estrone (E1).

Embodiment 57

The method according to any one of embodiments 45 to 53, wherein the substrate for HSD17B13 comprises an androgen hormone.

Embodiment 58

The method according to embodiment 57, wherein the androgen hormone comprises androstaendiol, testosterone, or dihydroxy testosterone (DHT).

Embodiment 59

The method according to any one of embodiments 45 to 53, wherein the substrate for HSD17B13 comprises an androgen hormone derivative.

Embodiment 60

The method according to embodiment 59, wherein the androgen hormone derivative comprises trilostane.

Embodiment 61

The method according to any one of embodiments 45 to 52, wherein the substrate for HSD17B13 comprises a fatty acid.

Embodiment 62

The method according to embodiment 61, wherein the fatty acid comprises ricinoleic acid.

Embodiment 63

The method according to any one of embodiments 45 to 52, wherein the substrate for HSD17B13 comprises a bioactive lipid.

Embodiment 64

The method according to embodiment 63, wherein the bioactive lipid comprises an eicosanoid.

Embodiment 65

The method according to embodiment 64, wherein the eicosanoid comprises a leukotriene.

Embodiment 66

The method according to embodiment 65, wherein the leukotriene comprises leukotriene B4.

Embodiment 67

The method according to any one of embodiments 45 to 66, wherein the HSD17B13 comprises human HSD17B13.

Embodiment 68

The method according to any one of embodiments 45 to 67, wherein the HSD17B13 comprises an amino acid sequence that is at least about 90% identical to SEQ ID NO:1.

Embodiment 69

The method according to any one of embodiments 45 to 68, wherein the HSD17B13 comprises the amino acid sequence of SEQ ID NO:1.

Embodiment 70

A method for screening a test compound for capability to inhibit hydroxysteroid (17-beta) dehydrogenase 13 (HSD17B13), comprising (a) contacting a first cell expressing HSD17B13 with a test compound and a substrate for HSD17B13, (b) contacting a second cell expressing HSD17B13 with a control and a substrate for HSD17B13, (c) determining the level of substrate product produced by the cell according to step (a) and according to step (b), and identifying the test compound as an inhibitor of HSD17B13 when the level of substrate product produced according to step (a) is lower than the level of substrate product produced according to step (b).

Embodiment 71

The method according to embodiment 70, wherein the first cell and the second cell are mammalian cells.

Embodiment 72

The method according to embodiment 71, wherein the mammalian cells are HEK 293 cells.

Embodiment 73

The method according to any one of embodiments 70 to 72, wherein the test compound comprises an organic compound.

Embodiment 74

The method according to any one of embodiments 70 to 72, wherein the test compound comprises an inorganic compound.

Embodiment 75

The method according to any one of embodiments 70 to 72, wherein the test compound comprises a biomolecule.

Embodiment 76

The method according to any one of embodiments 70 to 75, wherein the test compound is comprised in a composition comprising a carrier.

Embodiment 77

The method according to any one of embodiments 70 to 76, wherein the test compound is comprised in a composition comprising an excipient.

Embodiment 78

The method according to any one of embodiments 70 to 77, wherein the substrate for HSD17B13 comprises a steroid hormone or derivative thereof.

Embodiment 79

The method according to any one of embodiments 70 to 78, wherein the substrate for HSD17B13 comprises an estrogen hormone.

Embodiment 80

The method according to embodiment 79, wherein the estrogen hormone comprises estradiol (E2).

Embodiment 81

The method according to embodiment 79, wherein the estrogen hormone comprises estrone (E1).

Embodiment 82

The method according to any one of embodiments 70 to 78, wherein the substrate for HSD17B13 comprises an androgen hormone.

Embodiment 83

The method according to embodiment 82, wherein the androgen hormone comprises androstaendiol, testosterone, or dihydroxy testosterone (DHT).

Embodiment 84

The method according to any one of embodiments 70 to 78, wherein the substrate for HSD17B13 comprises an androgen hormone derivative.

Embodiment 85

The method according to embodiment 84, wherein the androgen hormone derivative comprises trilostane.

Embodiment 86

The method according to any one of embodiments 70 to 77, wherein the substrate for HSD17B13 comprises a fatty acid.

Embodiment 87

The method according to embodiment 86, wherein the fatty acid comprises ricinoleic acid.

Embodiment 88

The method according to any one of embodiments 70 to 77, wherein the substrate for HSD17B13 comprises a bioactive lipid.

Embodiment 89

The method according to embodiment 88, wherein the bioactive lipid comprises an eicosanoid.

Embodiment 90

The method according to embodiment 89, wherein the eicosanoid comprises a leukotriene.

Embodiment 91

The method according to embodiment 90, wherein the leukotriene comprises leukotriene B4.

Embodiment 92

The method according to any one of embodiments 70 to 91, wherein the HSD17B13 comprises human HSD17B13.

Embodiment 93

The method according to any one of embodiments 70 to 92, wherein the HSD17B13 comprises an amino acid sequence that is at least about 90% identical to SEQ ID NO:1.

Embodiment 94

The method according to any one of embodiments 70 to 93, wherein the HSD17B13 comprises the amino acid sequence of SEQ ID NO:1.

Embodiment 95

A complex, comprising an HSD17B13 protein and an HSD17B13 substrate.

Embodiment 96

The complex according to embodiment 95, further comprising $NAD^+$.

Embodiment 97

The complex according to embodiment 95 or 96, wherein the HSD17B13 substrate comprises a steroid hormone or derivative thereof.

Embodiment 98

The complex according to any one of embodiments 95 to 97, wherein the HSD17B13 substrate comprises an estrogen hormone.

Embodiment 99

The complex according to embodiment 98, wherein the estrogen hormone comprises estradiol (E2).

Embodiment 100

The complex according to embodiment 98, wherein the estrogen hormone comprises estrone (E1).

Embodiment 101

The complex according to any one of embodiments 95 to 97, wherein the HSD17B13 substrate comprises an androgen hormone.

Embodiment 102

The complex according to embodiment 101, wherein the androgen hormone comprises androstaendiol, testosterone, or dihydroxy testosterone (DHT).

Embodiment 103

The complex according to any one of embodiments 95 to 97, wherein the HSD17B13 substrate comprises an androgen hormone derivative.

Embodiment 104

The complex according to embodiment 103, wherein the androgen hormone derivative comprises trilostane.

Embodiment 105

The complex according to any one of embodiments 95 to 97, wherein the HSD17B13 substrate comprises a fatty acid.

Embodiment 106

The complex according to embodiment 105, wherein the fatty acid comprises ricinoleic acid.

Embodiment 107

The complex according to any one of embodiments 95 to 97, wherein the HSD17B13 substrate comprises a bioactive lipid.

Embodiment 108

The complex according to embodiment 107, wherein the bioactive lipid comprises an eicosanoid.

Embodiment 109

The complex according to embodiment 108, wherein the eicosanoid comprises a leukotriene.

Embodiment 110

The complex according to embodiment 109, wherein the leukotriene comprises leukotriene B4.

Embodiment 111

The complex according to any one of embodiments 95 to 110, wherein the HSD17B13 comprises human HSD17B13.

Embodiment 112

The complex according to any one of embodiments 95 to 111, wherein the HSD17B13 comprises an amino acid sequence that is at least about 90% identical to SEQ ID NO:1.

Embodiment 113

The complex according to any one of embodiments 95 to 112, wherein the HSD17B13 comprises the amino acid sequence of SEQ ID NO:1.

Embodiment 114

A composition, comprising the complex according to any one of embodiments 95 to 113 and a carrier.

Embodiment 115

A composition, comprising an HSD17B13 protein, an HSD17B13 substrate, and a carrier.

Embodiment 116

The composition according to embodiment 115, further comprising NAD$^+$.

Embodiment 117

The composition according to embodiment 115 or 116, wherein the HSD17B13 substrate comprises a steroid hormone or derivative thereof.

Embodiment 118

The composition according to any one of embodiments 115 to 117, wherein the HSD17B13 substrate comprises an estrogen hormone.

Embodiment 119

The composition according to embodiment 118, wherein the estrogen hormone comprises estradiol (E2).

Embodiment 120

The composition according to embodiment 118, wherein the estrogen hormone comprises estrone (E1).

Embodiment 121

The composition according to any one of embodiments 115 to 117, wherein the HSD17B13 substrate comprises an androgen hormone.

Embodiment 122

The composition according to embodiment 121, wherein the androgen hormone comprises androstaendiol, testosterone, or dihydroxy testosterone (DHT).

Embodiment 123

The composition according to any one of embodiments 115 to 117, wherein the HSD17B13 substrate comprises an androgen hormone derivative.

Embodiment 124

The composition according to embodiment 123, wherein the androgen hormone derivative comprises trilostane.

Embodiment 125

The composition according to any one of embodiments 115 to 117, wherein the HSD17B13 substrate comprises a fatty acid.

Embodiment 126

The composition according to embodiment 125, wherein the fatty acid comprises ricinoleic acid.

Embodiment 127

The composition according to any one of embodiments 115 to 117, wherein the HSD17B13 substrate comprises a bioactive lipid.

Embodiment 128

The composition according to embodiment 127, wherein the bioactive lipid comprises an eicosanoid.

Embodiment 129

The composition according to embodiment 128, wherein the eicosanoid comprises a leukotriene.

Embodiment 130

The composition according to embodiment 129, wherein the leukotriene comprises leukotriene B4.

Embodiment 131

The composition according to any one of embodiments 115 to 130, wherein the HSD17B13 comprises human HSD17B13.

Embodiment 132

The composition according to any one of embodiments 115 to 131, wherein the HSD17B13 comprises an amino acid sequence that is at least about 90% identical to SEQ ID NO:1.

Embodiment 133

The composition according to any one of embodiments 115 to 132, wherein the HSD17B13 comprises the amino acid sequence of SEQ ID NO:1.

Embodiment 134

A method for screening a test compound for capability to inhibit a hydroxysteroid (17-beta) dehydrogenase (HSD17B) family member protein, comprising: a) contacting a first HSD17B family member protein with a test compound, a substrate for the HSD17B family member protein, NAD$^+$, a pre-reduced form of luciferin, an enzyme that reduces the pre-reduced form of luciferin to produce luciferin, and luciferase; b) contacting a same second HSD17B family member protein with a control, a substrate for the HSD17B family member protein, NAD$^+$, a pre-reduced form of luciferin, an enzyme that reduces the pre-reduced form of luciferin to produce luciferin, and luciferase; c) detecting the emission wavelength of luciferin produced by the luciferase according to step a) and according to step b); and d) identifying the test compound as an inhibitor of the HSD17B family member protein when the emission wavelength of luciferin produced according to step a) is lower than the wavelength of luciferin produced according to step b).

Embodiment 135

The method according to embodiment 134, wherein the HSD17B family member protein is one or more of HSD17B1, HSD17B2, HSD17B3, HSD17B4, HSD17B5, HSD17B6, HSD17B7, HSD17B8, HSD17B9, HSD17B10, HSD17B11, HSD17B12, HSD17B13, or HSD17B14.

Embodiment 136

The method according to embodiment 134, wherein the HSD17B family member protein is one or more of HSD17B1, HSD17B2, HSD17B4, HSD17B5, HSD17B10, HSD17B11, or HSD17B13.

Embodiment 137

The method according to embodiment 134, wherein the HSD17B family member protein is HSD17B13.

Embodiment 138

The method according to embodiment 134, wherein the substrate for the HSD17B family member protein comprises a steroid hormone or derivative thereof.

Embodiment 139

The method according to embodiment 138, wherein the substrate for the HSD17B family member protein comprises an estrogen hormone.

Embodiment 140

The method according to embodiment 139, wherein the estrogen hormone comprises estradiol (E2).

Embodiment 141

The method according to embodiment 139, wherein the estrogen hormone comprises estrone (E1).

Embodiment 142

The method according to embodiment 138, wherein the substrate for the HSD17B family member protein comprises an androgen hormone.

Embodiment 143

The method according to embodiment 142, wherein the androgen hormone comprises androstaendiol, testosterone, or dihydroxy testosterone (DHT).

Embodiment 144

The method according to embodiment 138, wherein the substrate for the HSD17B family member protein comprises an androgen hormone derivative.

Embodiment 145

The method according to embodiment 144, wherein the androgen hormone derivative comprises trilostane.

Embodiment 146

The method according to embodiment 134, wherein the substrate for the HSD17B family member protein comprises a fatty acid.

Embodiment 147

The method according to embodiment 146, wherein the fatty acid comprises ricinoleic acid.

Embodiment 148

The method according to embodiment 134, wherein the substrate for the HSD17B family member protein comprises a bioactive lipid.

Embodiment 149

The method according to embodiment 148, wherein the bioactive lipid comprises an eicosanoid.

Embodiment 150

The method according to embodiment 149, wherein the eicosanoid comprises a leukotriene.

Embodiment 151

The method according to embodiment 150, wherein the leukotriene comprises leukotriene B4.

Embodiment 152

The method according to embodiment 137, wherein the first and second HSD17B family member protein is an HSD17B13 protein that comprises an amino acid sequence that is at least about 90% identical to SEQ ID NO:1.

Embodiment 153

The method according to embodiment 152, wherein the first and second HSD17B13 protein comprises the amino acid sequence of SEQ ID NO:1.

Embodiment 154

A kit comprising: a hydroxysteroid (17-beta) dehydrogenase (HSD17B) family member protein or a cell expressing an HSD17B family member protein; a substrate for the HSD17B family member protein; and instructions for using the HSD17B family member protein and substrate in a method for screening a test compound for capability to inhibit the HSD17B family member protein.

Embodiment 155

The kit according to embodiment 154, wherein the kit further comprises NAD$^+$, a pre-reduced form of luciferin, an enzyme that reduces the pre-reduced form of luciferin to produce luciferin, and luciferase.

Embodiment 156

A method for screening a test compound for capability to inhibit a hydroxysteroid (17-beta) dehydrogenase (HSD17B) family member protein, comprising: a) contacting a first cell expressing the HSD17B family member protein with a test compound and a substrate for the HSD17B family member protein; b) contacting a second cell expressing the same HSD17B family member protein with a control and a substrate for the HSD17B family member protein; c) determining the level of substrate depletion by the cell according to step a) and according to step b); and d) identifying the test compound as an inhibitor of the HSD17B family member protein when the level of substrate depletion according to step a) is lower than the level of substrate depletion produced according to step b).

Embodiment 157

A method for screening a test compound for capability to inhibit a hydroxysteroid (17-beta) dehydrogenase (HSD17B) family member protein, comprising: a) contacting a first cell expressing the HSD17B family member protein with a test compound and a substrate for the HSD17B family member protein; b) contacting a second cell expressing the same HSD17B family member protein with a control and a substrate for the HSD17B family member protein; c) determining the level of substrate product produced by the cell according to step a) and according to step b); and d) identifying the test compound as an inhibitor of the HSD17B family member protein when the level of substrate product produced according to step a) is lower than the level of substrate product produced according to step b).

Embodiment 158

A complex comprising an HSD17B family member protein and a substrate for the HSD17B family member protein.

Embodiment 159

A composition comprising a complex and a carrier, wherein the complex comprises an HSD17B family member protein and a substrate for the HSD17B family member protein.

Embodiment 160

A composition comprising an HSD17B family member protein, a substrate for an HSD17B family member protein, and a carrier.

The disclosure is not limited to the embodiments described and exemplified above, but is capable of variation and modification within the scope of the appended claims.

What is claimed is:

1. A kit comprising:
   a hydroxysteroid (17-beta) dehydrogenase 13 (HSD17B13) protein or a cell expressing an HSD17B13 protein;
   NAD+;
   a pre-reduced form of luciferin;
   an enzyme that reduces the pre-reduced form of luciferin to produce luciferin;
   luciferase;
   a substrate for the HSD17B13 protein chosen from a fatty acid or a bioactive lipid, wherein the substrate is labeled with a radiolabel, a fluorescent label, or colloidal gold; and
   instructions for using the HSD17B13 protein and substrate in a method for screening a test compound for capability to inhibit the HSD17B13 protein.

2. The kit according to claim 1, wherein the substrate for the HSD17B13 protein is a fatty acid.

3. The kit according to claim 2, wherein the fatty acid comprises ricinoleic acid.

4. The kit according to claim 1, wherein the substrate for the HSD17B13 protein is a bioactive lipid.

5. The kit according to claim 4, wherein the bioactive lipid comprises an eicosanoid.

6. The kit according to claim 5, wherein the eicosanoid comprises a leukotriene.

7. The kit according to claim 6, wherein the leukotriene comprises leukotriene B4.

* * * * *